（12） United States Patent
Yamashita

(10) Patent No.: US 11,312,720 B2
(45) Date of Patent: Apr. 26, 2022

(54) HYDROCHLORIDE SALT OF 2-((3R,4S)-1-(5-(4-CHLORO-3,5-DIFLUOROPHENYL)-7-((2-FLUORO-6-METHYLPHENYL)(METHYL)AMINO)PYRAZOLO[1,5-A]PYRIMIDINE-2-CARBONYL)-3-METHOXYPIPERIDIN-4-YL)ACETIC ACID AND CRYSTALS THEREOF

(71) Applicant: Eisai R&D Management Co., Ltd., Tokyo (JP)

(72) Inventor: Taro Yamashita, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/965,067

(22) PCT Filed: Feb. 22, 2019

(86) PCT No.: PCT/JP2019/006850
§ 371 (c)(1),
(2) Date: Jul. 27, 2020

(87) PCT Pub. No.: WO2019/163956
PCT Pub. Date: Aug. 29, 2019

(65) Prior Publication Data
US 2021/0107907 A1 Apr. 15, 2021

(30) Foreign Application Priority Data
Feb. 26, 2018 (JP) .............................. JP2018-031646

(51) Int. Cl.
*A61K 31/519* (2006.01)
*C07D 487/04* (2006.01)
(52) U.S. Cl.
CPC ........ *C07D 487/04* (2013.01); *C07B 2200/13* (2013.01)
(58) Field of Classification Search
CPC ........................... A61K 31/519; C07D 487/04
USPC ........................................ 514/259.3; 544/281
See application file for complete search history.

(56) References Cited

FOREIGN PATENT DOCUMENTS

| JP | 2003-286171 | 10/2003 |
|---|---|---|
| JP | 2004-170323 | 6/2004 |
| JP | 2013-060438 | 4/2013 |
| JP | 2013-520399 | 6/2013 |
| JP | 2014-514246 | 6/2014 |
| JP | 2016-531864 | 10/2016 |
| WO | WO 2003/037900 | 5/2003 |
| WO | WO 2005/030773 | 4/2005 |
| WO | WO 2011/105628 | 9/2011 |
| WO | WO 2012/101453 | 8/2012 |
| WO | WO 2015/048245 | 4/2015 |
| WO | WO 2018/043461 | 3/2018 |

OTHER PUBLICATIONS

Submission Document in European Patent Application No. 19757272.0, dated Nov. 23, 2020, 7 pages.
Submission Document in Chinese Patent Application No. 201980010733.4, dated Dec. 15, 2020, 10 pages (with English Translation).
Afkhami-Goli et al., "Proteinase-Activated Receptor-2 Exerts Protective and Pathogenic Cell Type-Specific Effects in Alzheimer's Disease," The Journal of Immunology, 2007, 179(8):5493-5503.
Böhm et al., "Molecular cloning, expression and potential functions of the human proteinase-activated receptor-2," Biochemical Journal, 1996, 314:1009-1016.
Dale et al., "Protease Signaling to G Protein-Coupled Receptors: Implications for Inflammation and Pain," Journal of Receptors and Signal Transduction, 2008, 28:29-37.
D'Andrea et al., "Characterization of protease-activated receptor-2 immunoreactivity in normal human tissues," Journal of Histochemistry & Cytochemistiy, 1998, 46(2):157-164.
Déry et al., "Proteinase-activated receptors: novel mechanisms of signaling by serine proteases," American Journal of Physiology-Cell Physiology, 1998, 274(6):C1429-C1452.
Hachem et al., "Serine Protease Signaling of Epidermal Permeability Barrier Homeostasis," Journal of Investigative Dermatology, 2006, 126(9):2074-2086.
Macfarlane et al. "Proteinase-activated receptors." Pharmacological Reviews, 2001, 53(2):245-282.
PCT International Search Report in International Application No. PCT/JP2019/006850, dated May 21, 2019, 2 pages.
Rothmeier et al., "Protease-activated receptor 2 signaling in inflammation," Seminars in Immunopathology, 2012, 34(1):133-149.

(Continued)

*Primary Examiner* — Douglas M Willis
(74) *Attorney, Agent, or Firm* — Fish & Richardson P.C.

(57) ABSTRACT

A salt of the compound represented by formula (1) and crystals thereof having the potential to be used as drug substances for pharmaceutical products.

(I)

14 Claims, 4 Drawing Sheets

(56) References Cited

OTHER PUBLICATIONS

Seyfarth et al., "Dry skin, barrier function, and irritant contact dermatitis in the elderly," Clinics in Dermatology, 2011, 29(1):31-36.
Yamaguchi et al., "Physiological factors that regulate skin pigmentation," J. Biofactors., 2009, 35(2):193-199.
Yau et al., "Toward drugs for protease-activated receptor 2 (PAR2)," Journal of Medicinal Chemistry, 2013, 56(19):7477-7497.
Submission Document in Israeli Patent Application No. 276160, dated Jun. 7, 2021, 4 pages (with English Translation).
PCT International Preliminary Report on Patentability in International Application No. PCT/JP2019/006850, dated Sep. 3, 2020, 7 pages.
Caira, "Crystalline Polymorphism of Organic Compounds," Topics in Current Chemistry, Springer Verlag, 1998, 198:163-208.
Search Report in European Patent Application No. 19757272.0, dated Sep. 22, 2021, 9 pages.
Office Action in Israeli Patent Application No. 276160, dated Mar. 21, 2021, 5 pages (with English Translation).
Submission Document in European Patent Application No. 19757272.0, dated Jan. 14, 2022, 7 pages.
Office Action in Russian Patent Application No. 2020125450, dated Feb. 22, 2022, 21 pages (with English Translation).

HYDROCHLORIDE SALT OF 2-((3R,4S)-1-(5-(4-CHLORO-3,5-DIFLUOROPHENYL)-7-((2-FLUORO-6-METHYLPHENYL)(METHYL)AMINO) PYRAZOLO[1,5-A]PYRIMIDINE-2-CARBONYL)-3-METHOXYPIPERIDIN-4-YL) ACETIC ACID AND CRYSTALS THEREOF

TECHNICAL FIELD

The present invention relates to a salt of a pyrazolo[1,5-a]pyrimidine compound having a PAR2 inhibitory action and crystals thereof.

BACKGROUND ART

Protease-activated receptor (PAR) is a type of trimeric U protein-coupled seven-transmembrane receptors and belongs to the receptor family mediating the cell action of serine proteases, and four molecules, PAR1, PAR2, PAR3 and PAR4, have been cloned so far.

Serine proteases cleave an extracellular amino-terminal peptide chain of the PAR molecule at a specific site and thus expose a new amino-terminal peptide chain having a receptor activation sequence consisting of 5 or 6 amino acid residues. The newly exposed amino-terminal peptide chain cleaved by a serine protease bonds as a chain-like ligand to the extracellular loop 2, which is the active site of PAR2 itself and thus activates PAR2. PAR2 is known to be activated by trypsin, tryptase, kallikrein (mainly kallikreins 2, 4, 5, 6 and 14), blood coagulation factor VIIa, blood coagulation factor Xa, and the like, and also activated when a synthetic peptide consisting of 5 or 6 amino acids synthesized based on the receptor activation sequence enters exogenously (see Non Patent Literatures 1 to 3).

PAR2 herein is widely distributed in vivo such as blood vessel, prostate gland, small intestine, large intestine, liver, kidney, pancreas, stomach, lung, brain and skin, and known to be an aggravating factor in various diseases such as neurogenic inflammation, pain, itch, inflammation and allergy (see Patent Literatures 1 and 2, and Non Patent Literatures 4 to 6). For this reason, a PAR2 inhibitor is expected to be a possible treatment drug for these diseases and suggested to be, for example, a treatment drug for inflammatory bowel diseases, a treatment drug for dermatitis, a treatment drug for allergic diseases, or a preventive drug for skin pigmentation (see Patent Literatures 3 to 5 and Non Patent Literatures 3 and 6 to 11).

CITATION LIST

Patent Literature

[Patent Literature 1] JP-A-2003-286171
[Patent Literature 2] JP-A-2004-170323
[Patent Literature 3] WO 2012/101453
[Patent Literature 4] WO 2015/048245
[Patent Literature 5] WO 2005/030773

Non Patent Literature

[Non Patent Literature 1] Dery, O. et al. Am. J. Physiol (Cell Physiol.) 274, C1429-1452, 1998
[Non Patent Literature 2] Macfarlane, S. R et al. Pharmacol. Rev. 53, 245-282, 2001
[Non Patent Literature 3] Yau, M K. et al. Journal of Medicinal Chemistry, 56, 7477-7497, 2013
[Non Patent Literature 4] Bohm, S. K. et al. Biochem. J. 15; 314, 1009-1016, 19%
[Non Patent Literature 5] D'Andrea, M. R et al. J. Histochem. Cytochem. 46(2): 157-164, 1998
[Non Patent Literature 6] Rothmeier, A. S., Ruf, W. Semin. Immunopathol. 34(1): 133-149, 2012
[Non Patent Literature 7] Yamaguchi, Y, Hearing, V. J. Biofactors. 35(2): 193-199, 2009
[Non Patent Literature 8] Afkhami-Goli, A. et al. The Journal of Immunology. 179: 5493-5503, 2007
[Non Patent Literature 9] Dale, C. et al. Journal of Receptors and Signal Transduction. 28:29-37, 2008
[Non Patent Literature 10] Hachem, J. P. et al. Journal of Investigative Dermatology. 126: 2074-2086, 2006
[Non Patent Literature 11] Seyfarth, F. et al. Clinics in Dermatology. 29: 31-36, 2011

SUMMARY OF INVENTION

Technical Problem

A compound (2-((3R,4S)-1-(5-(4-chloro-3,5-difluorophenyl)-7-((2-fluoro-6-methylphenyl)(methyl)amino) pyrazolo [1,5-a]pyrimidine-2-carbonyl)-3-methoxypiperidin-4-yl) acetic acid, hereinafter also referred to as "Compound (I)") represented by the following formula (I) has a PAR2 inhibitory action and has the potential to be used as an inflammatory skin disease treatment agent or an inflammatory bowel disease treatment agent.

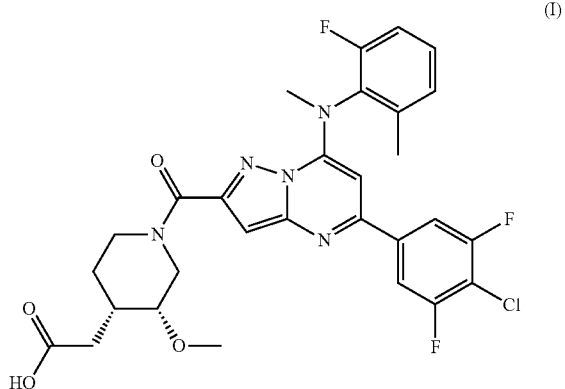 [SMILES: CO[C@H]1CN(C(=O)c2cc3nc(-c4cc(F)c(Cl)c(F)c4)cc(N(C)c4c(C)cccc4F)n3n2)CC[C@H]1CC(=O)O]

Generally, properties of compounds useful as pharmaceutical products, salts thereof or crystals of the salts impose significant impacts on the bioavailability of drugs, the purity of drug substances, the formulation of preparations and the like.

Solution to Problem

The present inventors earnestly conducted studies on Compound (I) in consideration of the above circumstances and consequently found a salt of Compound (I) or crystals thereof, whereby the present invention was accomplished.

More specifically, the present invention relates to the following [1] to [14].

[1] A hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid represented by formula (I).

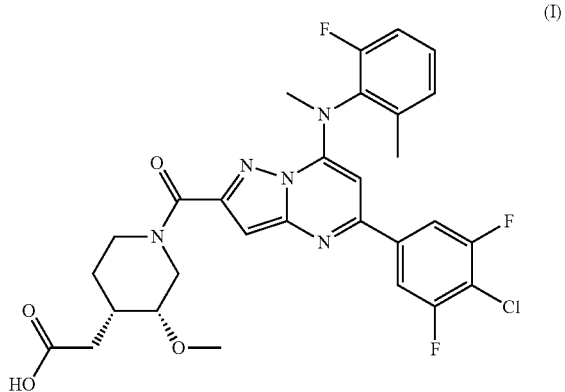 [SMILES: CO[C@H]1CN(C(=O)c2cc3nc(-c4cc(F)c(Cl)c(F)c4)cc(N(C)c4c(C)cccc4F)n3n2)CC[C@H]1CC(=O)O]

[2] A crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid represented by formula (I).

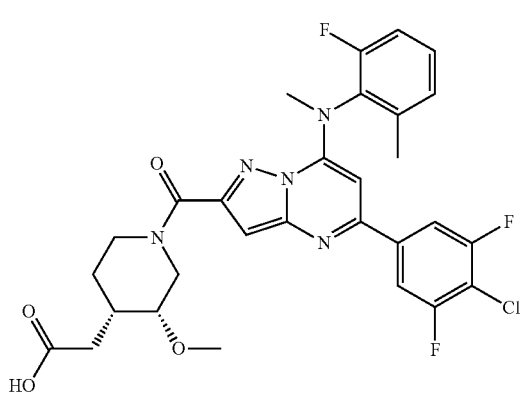

[3] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having a diffraction peak at a diffraction angle (2θ±0.2°) 8.3° in powder X-ray diffractometry.

[4] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having diffraction peaks at diffraction angles (2θ±0.2°) 8.3° and 13.1° in powder X-ray diffractometry.

[5] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having diffraction peaks at diffraction angles (2θ±0.2°) 8.3°, 13.1° and 15.7° in powder X-ray diffractometry.

[6] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having diffraction peaks at diffraction angles (2θ±0.2°) 8.3°, 11.4°, 13.1°, 15.7° and 17.3° in powder X-ray diffractometry.

[7] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having diffraction peaks at diffraction angles (2θ±0.2°) 8.3°, 11.4°, 13.1°, 15.2°, 15.7°, 17.3°, 18.8°, 19.7°, 22.3° and 25.0° in powder X-ray diffractometry.

[8] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having a powder X-ray diffraction pattern substantially identical to the powder X-ray diffraction pattern shown in FIG. 1.

[9] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having peaks at chemical shifts (δ±0.5 ppm) 58.4 ppm, 77.4 ppm and 173.5 ppm in a solid state $^{13}C$ NMR spectrum.

[10] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having peaks at chemical shifts (δ±0.5 ppm) 18.5 ppm, 58.4 ppm, 77.4 ppm, 94.4 ppm and 173.5 ppm in a solid state $^{13}C$ NMR spectrum.

[11] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having peaks at chemical shifts (δ±0.5 ppm) 18.5 ppm, 19.9 ppm, 56.6 ppm, 58.4 ppm, 76.2 ppm, 77.4 ppm, 94.4 ppm, 95.9 ppm, 129.3 ppm and 173.5 ppm in a solid state $^{13}C$ NMR spectrum.

[12] The crystal according to [2], the crystal of a hydrochloride of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid having a solid state $^{13}C$ NMR spectrum substantially identical to the solid state $^{13}C$ NMR spectrum shown in FIG. 2.

[13] A pharmaceutical composition comprising the salt according to [1] as an active ingredient.

[14] A pharmaceutical composition comprising the crystal according to any one of [2] to [12] as an active ingredient.

Advantageous Effects of Invention

A salt of Compound (I) and crystals thereof provided by the present invention have the potential to be used as drug substances for pharmaceutical products.

DESCRIPTION OF EMBODIMENTS

Figure 1:
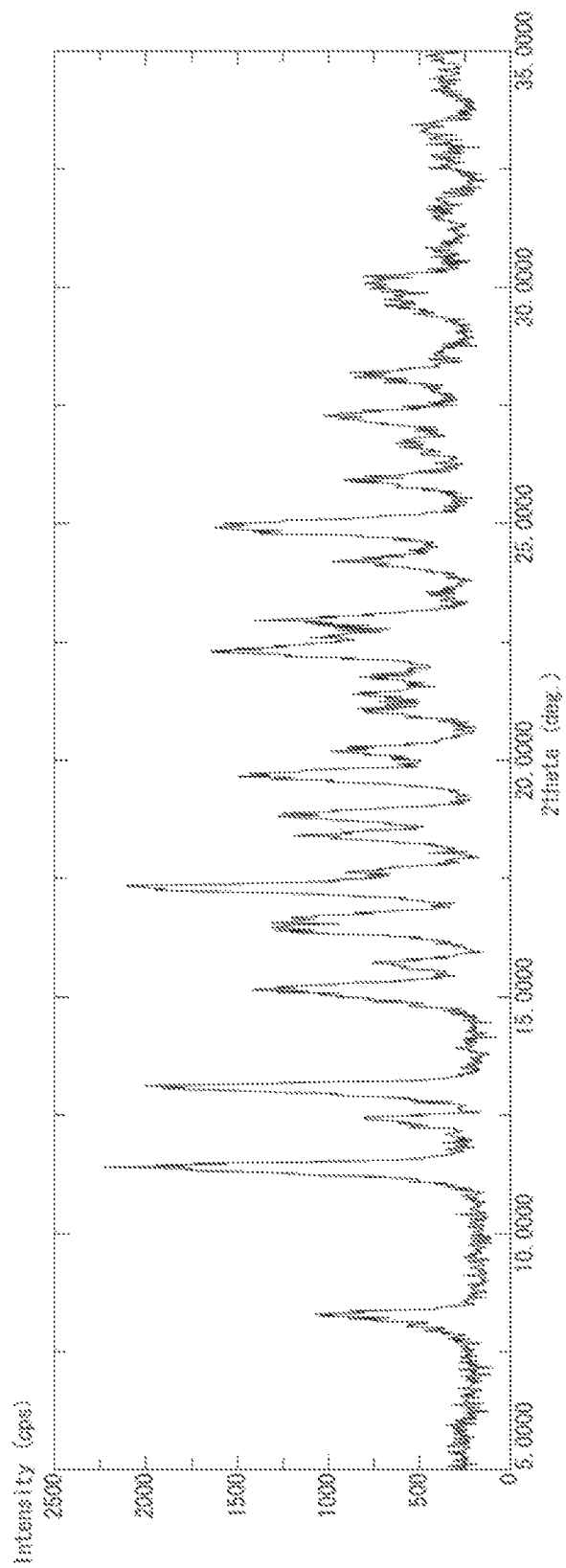
FIG. 1 is a powder X-ray diffraction pattern of crystals of a hydrochloride of Compound (I) obtained in Example 1. The abscissa shows the diffraction angle (2θ) and the ordinate shows the peak intensity.

Hereinafter, a salt of Compound (1) and crystals thereof of the present invention, and a production method thereof will be described in detail.

The "salt" in the present specification means a chemical substance consisting of Compound (I) and a specific equivalent number of acid or base to Compound (I).

The salt is not particularly limited as long as it is pharmaceutically acceptable, but specific examples include inorganic acid salts (e.g., hydrochloride, hydrobromide, sulfate, nitrate and phosphate), organic acid salts (e.g., acetate, succinate, fumarate, maleate, tartrate, citrate, lactate, stearate, benzoate, mandelate, methanesulfonate, ethanesulfonate, p-toluenesulfonate and benzenesulfonate), acidic amino acid salts (e.g., aspartate and glutamate), inorganic basic salts (e.g., alkali metal salts such as sodium salt and potassium salt, alkaline earth metal salts such as calcium salt and magnesium salt, aluminum salt and ammonium salt), organic basic salts (e.g., diethylamine salt, diethanolamine salt, meglumine salt and N,N-dibenzylethylenediamine salt) and basic amino acid salts (e.g., arginine salt, lysine salt and ornithine salt).

The salt of the present invention may be a solvate. The solvate of a salt of Compound (I) in the present specification refers to a solid formed together by a salt of Compound (I) and crystals thereof and solvent molecules. Examples of the solvent for a solvate include ketone solvents such as acetone, 2-butanone, and cyclohexanone; ester solvents such as methyl acetate and ethyl acetate; ether solvents such as 1,2-dimethoxyethane and t-butyl methyl ether; alcohol solvents such as methanol, ethanol, 1-propanol and isopropanol; polar solvents such as N-methyl-2-pyrrolidone, N,N-dimethylformamide and dimethyl sulfoxide; and water.

The "crystal" in the present specification refers to crystals of Compound (I) or a salt thereof. Thus, for example, the crystal of a hydrochloride of Compound (1) is crystals of a salt formed by Compound (I) and hydrochloric acid and means crystals of a salt containing one molecule of hydrochloric acid to one molecule of Compound (I).

Examples of the preferable crystal of a salt of Compound (I) in the present specification include the crystal of a hydrochloride of Compound (I) having a diffraction peak at a diffraction angle (2θ±0.2°) 8.3° in powder X-ray diffractometry;

the crystal of a hydrochloride of Compound (I) having diffraction peaks at diffraction angles (2θ±0.2°) 8.3° and 13.1° in powder X-ray diffractometry;

the crystal of a hydrochloride of Compound (I) having diffraction peaks at diffraction angles (2θ±0.2°) 8.3°, 13.1° and 15.7° in powder X-ray diffractometry;

the crystal of a hydrochloride of Compound (I) having diffraction peaks at diffraction angles (2θ±0.2°) 8.3°, 11.4°, 13.1°, 15.7° and 17.3° in powder X-ray diffractometry;

the crystal of a hydrochloride of Compound (I) having diffraction peaks at diffraction angles (2θ±0.2°) 8.3°, 11.4°, 13.1°, 15.2°, 15.7°, 17.3°, 18.8°, 19.7°, 22.3° and 25.0° in powder X-ray diffractometry;

the crystal of a hydrochloride of Compound (I) having peaks at chemical shifts (δ±0.5 ppm) 58.4 ppm, 77.4 ppm and 173.5 ppm in a solid state $^{13}$C NMR spectrum;

the crystal of a hydrochloride of Compound (I) having peaks at chemical shifts (δ±0.5 ppm) 18.5 ppm, 58.4 ppm, 77.4 ppm, 94.4 ppm and 173.5 ppm in a solid state $^{13}$C NMR spectrum; and the crystal of a hydrochloride of Compound (I) having peaks at chemical shifts (δ±0.5 ppm) 18.5 ppm, 19.9 ppm, 56.6 ppm, 58.4 ppm, 76.2 ppm, 77.4 ppm, 94.4 ppm, 95.9 ppm, 129.3 ppm and 173.5 ppm in a solid state $^{13}$C NMR spectrum.

The diffraction peaks in powder X-ray diffractometry and the chemical shifts in a solid state $^{13}$C NMR spectrum described above are each distinctive to the crystals of a hydrochloride of Compound (I) and the peaks are characteristic with such crystals.

Generally, as a diffraction angle (2θ) in powder X-ray diffractometry may cause an error within a range of ±0.2°, the above values of diffraction angles need to be understood to include the numerical values within the ranges of about ±0.2°. Thus, in a specific compound, not only the crystals in which the diffraction angles of the peaks completely match in powder X-ray diffractometry but the crystals in which the diffraction angles of the peaks match with an error of about ±0.2° are also identical and included in the present invention.

For example, the "having a diffraction peak at a diffraction angle (2θ±0.2°) 8.3°" in the present specification means "having a diffraction peak at diffraction angles (2θ) 8.1° to 8.5°", and the cases with other diffraction angles are also the same.

Additionally, generally, the peak intensity or half-value width of a diffraction angle (2θ) in powder X-ray diffractometry varies at each measurement depending on differences in measurement conditions and nonuniformity in the size and shape of each particle of powder crystals used as a measurement sample despite the crystal forms being identical, and a constant peak intensity or half-value width is not necessarily always shown. For this reason, in the comparison of powder X-ray diffraction patterns, even when there are differences in the peak intensity or half-value width at the same diffraction angle (2θ), such differences do not mean that the measured crystal forms are different from each other. Thus, crystals of the compound showing powder X-ray diffraction patterns having such differences from the characteristic diffraction peaks of the specific crystal of the present invention mean the identical crystal form to crystals of the compound of the present invention. Additionally, the "having a powder X-ray diffraction pattern substantially identical to the powder X-ray diffraction pattern shown in FIG. 1" in the present specification means that not only a case in which a powder X-ray diffraction pattern having certain characteristic diffraction peaks completely corresponds with the powder X-ray diffraction pattern shown in FIG. 1 but a case in which peak intensities or half-value widths are different or diffraction angles of characteristic diffraction peaks correspond within an error range of ±0.2° is also the powder X-ray diffraction pattern identical to the powder X-ray diffraction pattern shown in FIG. 1. Thus, all crystals having such powder X-ray diffraction patterns mean the crystals identical to the crystal of the present invention.

The "chemical shifts (δ±0.5 ppm) 18.5 ppm, 19.9 ppm, 56.6 ppm, 58.4 ppm, 76.2 ppm, 77.4 ppm, 94.4 ppm, 95.9 ppm, 129.3 ppm and 173.5 ppm" in the present specification means "having substantially equivalent peaks at chemical shifts (δ±0.5 ppm) 18.5 ppm, 19.9 ppm, 56.6 ppm, 58.4 ppm, 76.2 ppm, 77.4 ppm, 94.4 ppm, 95.9 ppm, 129.3 ppm and 173.5 ppm, respectively, when solid state $^{13}$C NMR spectrum measurement is carried out under typical measurement conditions or the conditions described in the present specification."

When determining whether or not "having substantially equivalent peaks", generally, as a chemical shift 5 in a solid state $^{13}$C NMR spectrum may cause an error within a range of ±0.5 ppm, the above values of chemical shifts need to be understood to include the numerical values within the ranges of about ±0.5 ppm. Thus, not only the crystals in which the chemical shifts completely correspond in a solid state $^{13}$C NMR spectrum but the crystals in which chemical shifts correspond with an error of about ±0.5 ppm are also included in the present invention. For this reason, for example, the "having a peak at a chemical shift (δ±0.5 ppm) 173.5 ppm" in the present specification means having a peak at chemical shifts (δ) ranging from 173.0 ppm to 174.0 ppm", and the cases with other chemical shifts in a solid state $^{13}$C NMR spectrum are also the same. Additionally, the "crystals having a solid state $^{13}$C NMR spectrum substantially identical to the solid state $^{13}$C NMR spectrum shown in FIG. 2" means that not only a case in which solid state $^{13}$C NMR spectrum having peaks at certain chemical shifts completely corresponds with the solid state $^{13}$C NMR spectrum shown in FIG. 2 but a case in which peak intensities are different or characteristic peaks correspond within a range of about chemical shifts ±0.5 ppm is also crystals having the solid state $^{13}$C NMR spectrum identical to the solid state $^{13}$C NMR spectrum shown in FIG. 2. Thus, all crystals having such solid state $^{13}$C NMR spectrums mean the crystals identical to the crystal of the present invention.

Hereinafter, a production method of a salt of Compound (I), crystals thereof or the like, an embodiment of the present invention, will be described.

Production Method of Compound (I)

Compound (I) may be those produced by a method well known by those skilled in the art. For example, Compound (I) can be synthesized by the method described in Reference Example 2 to be described later.

Production Method of a Salt of Compound (I)

A salt of Compound (I) can be obtained by a typical method for producing a salt. Specifically, for example, Compound (I) is suspended or dissolved in a solvent while raising temperature as necessary, subsequently an acid or a base selected from the group consisting of inorganic acid salts, organic acid salts, acidic amino acid salts, inorganic basic salts, organic basic salts and basic amino acid salts is added to the suspension or solution to be obtained and stirred from several minutes to several days at room temperature or while cooling in an ice bath or allowed to stand from several minutes to several days at room temperature or while cooling in an ice bath to produce a salt of Compound (I). Using these production methods, a salt of Compound (I) can be obtained as crystalline or amorphous. Examples of the solvent used herein include alcohol solvents such as ethanol, 1-propanol and isopropanol; acetonitrile; ketone solvents such as acetone and 2-butanone; ester solvents such as ethyl acetate; saturated hydrocarbon solvents such as hexane and heptane; ether solvents such as t-butyl methyl ether or water. These solvents may be used singly, or 2 or more may be mixed and used.

A salt of Compound (I) can also be produced continuously, after synthesis of Compound (I) in the production method of Compound (I) described above, by employing the method described above.

Production method of crystals of Compound (1) or a salt thereof

Hereinafter, a production method of crystals of Compound (I) or a salt thereof will be described. Crystals of Compound (I) or a salt thereof can also be produced by dissolving Compound (I) or a salt thereof in a solvent with heating and cooling with stirring to crystallize.

Compound (I) or a salt thereof used for crystallization may be in any form, may be a solvate, a hydrate or an anhydride, may be amorphous or crystalline (including those consisting of a plurality of crystal polymorphs) and may be a mixture thereof Examples of the solvent used for crystallization include alcohol solvents such as methanol, ethanol, 2-propanol, 1-propanol and 1-butanol; acetonitrile; amide solvents such as N,N-dimethylformamide; ester solvents such as ethyl acetate; saturated hydrocarbon solvents such as hexane and heptane; ketone solvents such as acetone and 2-butanone; ether solvents such as t-butyl methyl ether or water. Additionally, these solvents may be used singly, or 2 or more may be mixed and used.

An amount of a solvent used can be suitably selected with the lower limit being an amount in which Compound (I) or a salt thereof dissolves by heating or an amount in which a suspension becomes storable and the upper limit being an amount in which a yield of crystals does not notably reduce.

In the crystallization, crystals of desired Compound (I) or a salt thereof may be added as seed crystals. A temperature of the solution at which seed crystals are added is not particularly limited and is preferably 0 to 80° C.

The temperature, when Compound (I) or a salt thereof is heated and dissolved, may be a temperature suitably selected in accordance with a solvent at which Compound (I) or a salt thereof dissolves, and is preferably a range from 50° C. to a temperature at which a solvent starts refluxing, and more preferably 55 to 80° C.

It is preferable to carry out cooling during the crystallization by suitably adjusting a cooling rate considering impacts on the quality, grain size, and the like, of crystals because rapid cooling may give those containing crystals (polymorphs) of different states. A preferable cooling rate is, for example, 5 to 40° C./hour.

Additionally, the final crystallization temperature can be suitably selected from the yield, quality and the like of crystals, and is preferably −25 to 30° C.

The crystallized crystals can be separated by a typical filtration operation to obtain the crystals of interest. The crystals separated by filtration are washed with the solvent as necessary and may further be dried. The solvent used for washing the crystals can be the same as the crystallization solvents. Preferably, examples include ethanol, acetone, 2-butane, ethyl acetate, diethyl ether, t-butyl methyl ether and hexane. Additionally, these solvents may be used singly, or 2 or more may be mixed and used.

The crystals separated by the filtration operation can be suitably left under the atmosphere or a nitrogen gas stream, or heated, to dry.

As the drying time, the time until the residual solvent becomes less than a predetermined amount may be appropriately selected according to the production amount, the drying device, the drying temperature and the like. Additionally, drying can also be carried out under ventilation or under reduced pressure. The degree of reduced pressure may be suitably selected in accordance with production amount, drying apparatus, drying temperature, and the like. The obtained crystals can also be left in the atmosphere as necessary after dried.

The salt of Compound (I) or crystals thereof obtained by the production method described above have the PAR2 inhibitory action as shown in the activity data in pharmacological Test Examples to be described later and, for example, have the potential to be used as drug substances for pharmaceutical products such as an inflammatory skin disease treatment agent or an inflammatory bowel disease treatment agent.

[Pharmaceutical Composition]

Another embodiment of the present invention is a pharmaceutical composition comprising a salt of Compound (I) or crystals thereof and pharmaceutically acceptable additives. The pharmaceutical composition can be produced by mixing pharmaceutically acceptable additives with a salt of Compound (I) or crystals thereof. The pharmaceutical composition according to the present invention can be produced in accordance with a known method described in, for example, General Rules for Preparations in The Japanese Pharmacopoeia Sixteenth Edition.

The pharmaceutical composition according to the present embodiment can be suitably administered to a patient in accordance with the dosage form thereof.

The dose of a salt of Compound (I) according to the present invention or crystals thereof varies depending on the level of symptoms, age, sex, body weight, administration form/kind of salt and the specific type of a disease, but is typically administered to an adult by oral administration in about 30 μg to 10 g, preferably 100 μg to 5 g, further preferably 100 μg to 1 g, a day, or by injection administration in about 30 μg to 1 g, preferably 100 μg to 500 mg, further preferably 100 μg to 300 mg, respectively once or in several divided doses.

EXAMPLES

Hereinafter, the present invention will be described in detail in reference with Reference Examples and Examples, but the present invention is not limited to these Reference Examples and Examples.

In the powder X-ray crystal diffractometry of the crystals produced in the following Reference Examples and Examples, the obtained crystals were put on a sample table of a powder X-ray diffractometer and analyzed under the following conditions.
(Measurement Conditions)
Sample holder: Aluminum holder
Target: Copper
Detector: Scintillation counter
Tube voltage: 50 kV
Tube current: 300 mA
Slit: Divergence slit 0.5 mm, scattering slit open, receiving slit open
Scanning speed: 5°/min or 10°/min
Sampling interval: 0.02°
Scanning range: 5 to 35°
Solid state $^{13}C$ NMR spectrum of the crystals were measured under the following conditions.
(Measurement Conditions)
Apparatus used: Avance 400 MHz (manufactured by BRUKER) 7 mm-CPMAS probe (manufactured by BRUKER)
Measurement nucleus: $^{13}C$ (100.6130636 MHz)
Measurement temperature: Room temperature (25° C.)
Pulse mode: CPTOSS Measurement (spinning sideband suppression method)
Rotation speed: 5000 Hz
Pulse repetition period: 3 sec
Contact time: 1 msec
Accumulated number of times: 3072 times
Reference substance: glycine (External reference: 176.03 ppm)

Compounds with a literature name, or the like, indicate that they were produced in accordance with the literature, or the like.

Additionally, the abbreviations used in the present specification are common abbreviations well known by those skilled in the art. In the present specification, the following abbreviations are used.
DMF: N,N-Dimethylformamide
DMSO: Dimethyl sulfoxide
DMSO-$d_6$: Deuterated dimethyl sulfoxide
HATU: 0-(7-Azabenzotriazol-1-yl)-N,N,N,N-tetramethyluronium hexafluorophosophate
HOBT: 1-Hydroxybenzotriazole
NMP: 1-Methyl-2-pyrrolidone
$Pd_2DBA_3$: Tris(dibenzylideneacetone)dipalladium
t-: Tertiary
THF: Tetrahydrofuran
WSC: 1-Ethyl-3-(3-dimethylaminopropyl)-carbodiimide hydrochloride
$^1$H-NMR: Proton nuclear magnetic resonance spectrometry The chemical shift of the proton nuclear magnetic resonance spectrum is recorded in δ unit (ppm) relative to tetramethylsilane and the coupling constant is recorded in hertz (Hz). Splitting patterns are as follows.
s; singlet, d; doublet, t; triplet, q; quartet, br; broad, m; multiplet, dd; double doublet, td; triple doublet.

$^1$H-NMR was measured using a Varian MERCURY plus model nuclear magnetic resonance apparatus (400 MHz), a Varian INOVA UNITY model nuclear magnetic resonance apparatus (400 MHz), a Varian INOVA UNITY model nuclear magnetic resonance apparatus (500 MHz) or a Bruker Avance model nuclear magnetic resonance apparatus (600 MHz).

The optical rotation was measured using a JASCO DIP-1000 model polarimeter.

For the chromatography, the silica gel used was either Merck Silica Gel 60 (70-230 mesh ASTM), Fuji Silysia Chemical Ltd. PSQ60B, Kanto Kagaku Silica Gel 60 (spherical, 40-50 μM) or YMC YMC*GEL ODS-A (12 nM S-50 μM), or a pre-packed column {column: YAMAZEN Hi-Flash™ Column (Silicagel), size; either S (16×60 mm), M (20×75 mm), L (26×100 mm), 2L (26×150 mm) or 3L (46×130 mm)} was used.

NH silica gel used was either Fuji Silysia Chemical Ltd. CHROMATOREX NH-DM2035 or a pre-packed column {column: YAMAZEN Hi-Flash™ Column (Amino), size; either S (16×60 mm), M (20×75 mm), L (26×100 mm), 2L (26×150 mm) or 3L (46×130 mm) or a Wako Pure Chemical Industries, Ltd. Presep™ (Luer Lock) NH2 (HC), size; type M (14 g/25 mL), type L (34 g/70 mL), type 2L (50 g/100 mL), type 3L (110 g/200 mL)}.

The "room temperature" in the following Examples and Reference Examples typically indicates about 10° C. to about 35° C. The "Vo" indicates a weight percent unless otherwise specified.

The chemical names for the compounds in the following Examples and Reference Examples were created based on the chemical structures using "E-Notebook" version 12 (PerkinElmer Co., Ltd.). However, the "*" in the configuration represents a relative position and indicates either one of the enantiomers unless otherwise specified. Further, in the case where "(3R*,4S*)" is written, the relative relationship of each stereocenter is indicated. More specifically, the "(3R*,4S*)" indicates either one of the specific enantiomers (3R,4S) or (3S,4R).

The mixture of rotamers in the present specification means a mixture of isomers having different conformations caused by intramolecular rotations around single bonds such as C—C, C—N and C—O.

Reference Example 1

Synthesis of 2-((3R*,4S*)-3-methoxypiperidin-4-yl)acetic Acid Ethyl Ester Hydrochloride

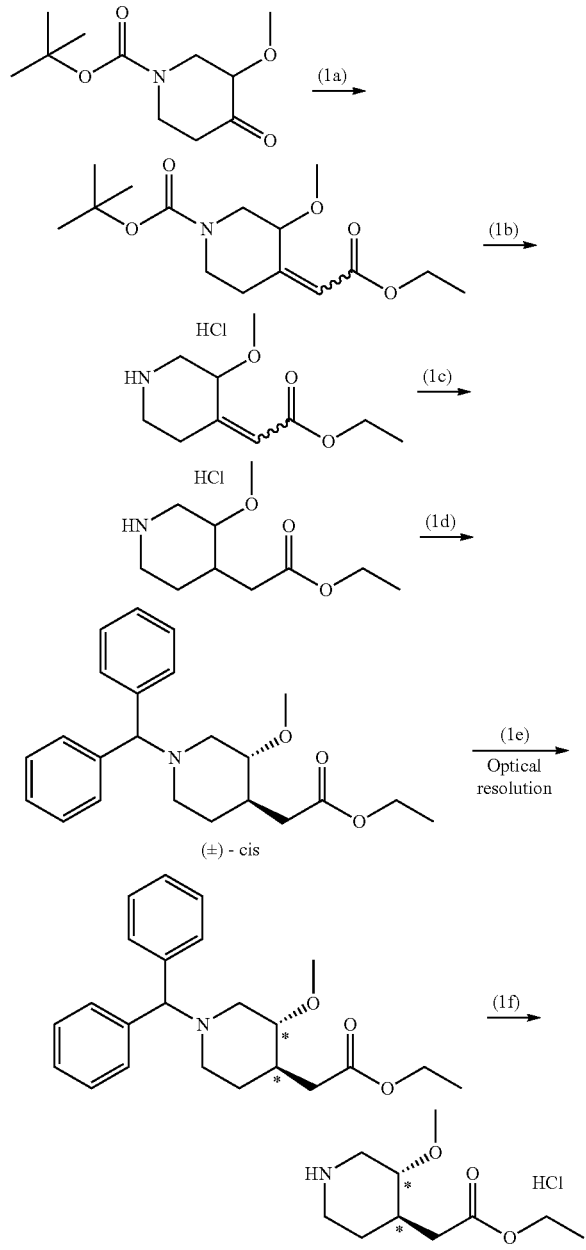

(1a) Synthesis of 4-((2-ethoxy-2-oxoethylidene)-3-methoxypiperidine-1-carboxylic Acid t-butyl Ester Under a nitrogen atmosphere at room temperature, sodium hydride (about 60%, 2.95 g) was added to a solution of ethyl diethylphosphonoacetate (16.56 g) in THF (340 mL), stirred for 15 minutes, subsequently a solution of 3-methoxy-4-oxopiperidine-1-carboxylic acid t-butyl ester (14.11 g) (WO 2012/080735) in tetrahydrofuran (50 mL) was added dropwise and stirred at room temperature for 16 hours. Ethyl acetate (1000 mL) and a saturated sodium hydrogen carbonate aqueous solution (400 mL) were added to the reaction mixture. The organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (14.65 g).

$^1$H-NMR (400 MHz, CDCl$_3$, E/Z mixture) δ: 1.29 (t, J=7.3 Hz, 3H), 1.47 (s, 4.5H), 1.48 (s, 4.5H), 1.98 (m, 0.5H), 2.52-2.83 (m, 2H), 3.2-3.97 (m, 3H), 3.30 (s, 1.5H), 3.37 (s, 1.5H), 3.80-4.58 (m, 1H), 4.18 (m, 2H), 5.21 (br.s, 0.5H), 5.83 (s, 0.5H), 5.94 (s, 0.5H).

(1b) Synthesis of 2-(3-methoxypiperidin-4-ylidene)acetic Acid Ethyl Ester Hydrochloride Tri fluoroacetic acid (4 mL) was added to a solution of 4-(2-ethoxy-2-oxoethylidene)-3-methoxypiperidine-1-carboxylic acid t-butyl ester (1.20 g) in dichloromethane (20 mL) and the mixture was stirred at room temperature for 5 hours. The reaction mixture was concentrated under reduced pressure, toluene (100 mL) was added thereto and concentrated under reduced pressure. Toluene (10 mL) was added again, the reaction mixture was concentrated under reduced pressure, subsequently ethyl acetate (10 mL), toluene (10 mL) and a 4N hydrogen chloride ethyl acetate solution (5 mL) were added to the residue and concentrated under reduced pressure, to obtain the title compound (0.95 g).

$^1$H-NMR (400 MHz, CDCl$_3$) δ: 1.29 (t, J=7 Hz, 1.5H), 1.29 (t, J=7 Hz, 1.5H), 2.92-3.20 (m, 3H), 3.33 (s, 1.5H), 3.34 (s, 1.5H), 3.25-3.91 (m, 4H), 4.16-4.24 (m, 2H), 5.98 (s, 0.5H), 6.00 (s, 0.5H), 7.95 (br.s, 0.5H), 8.43 (br.s, 0.5H), 10.11 (br.s, 1H).

(1c) Synthesis of 2-(3-methoxypiperidin-4-yl)acetic Acid Ethyl Ester Hydrochloride Palladium-activated carbon (Pd 10%) (0.21 g) was added to a mixture of 2-(3-methoxypiperidin-4-ylidene)acetic acid ethyl ester hydrochloride (0.95 g), ethanol (10 mL) and ethyl acetate (10 mL) and stirred at room temperature for 17 hours under a hydrogen atmosphere. The atmosphere was returned to nitrogen, the mixture was filtered through Celite and the Celite was washed with ethanol. The filtrate and the washing solution were combined and concentrated under reduced pressure, to obtain the title compound (1.02 g, mostly cis isomer).

$^1$H-NMR (400 MHz, CDCl$_3$, cis isomer) δ: 1.27 (t, J=7 Hz, 3H), 1.71 (br.d, J=14 Hz, 1H), 1.94 (br.q, J=14 Hz, 1H), 2.15 (m, 1H), 2.32 (dd, J=16, 6 Hz, 1H), 2.54 (dd, J=16, 8 Hz, 1H), 2.94 (m, 2H), 3.41 (s, 3H), 3.44-3.65 (m, 3H), 4.15 (q, J=7 Hz, 2H), 7.84 (br.s, 1H), 9.92 (br.s, 1H).

(1d) Synthesis of (±)-2-(cis-1-benzhydryl-3-methoxypiperidin-4-yl)acetic Acid Ethyl Ester Under a nitrogen atmosphere, at −20° C., a solution of bromodiphenylmethane (2.62 g) in DMF (5 mL) was added to a mixture of 2-(3-methoxypiperidin-4-yl)acetic acid ethyl ester hydrochloride (2.098 g), DMF (80 mL), triethylamine (1.35 mL) and potassium carbonate (2.44 g) and stirred at room temperature overnight. t-Butyl methyl ether (400 mL) and water (200 mL) were added thereto. The organic layer was washed sequentially with water (200 mL×2) and a saturated sodium chloride aqueous solution (200 mL) and dried over anhydrous magnesium sulfate. The drying agent was filtered off and the filtrate was concentrated under reduced pressure. The residue was purified by silica gel column chromatography (heptane-ethyl acetate system), to obtain the title compound (1.127 g) as a colorless liquid.

$^1$H-NMR (400 MHz, CDCl$_3$) δ: 1.24 (t, J=7 Hz, 3H), 1.51 (m, 1H), 1.69 (m, 1H), 1.94-2.12 (m, 3H), 2.27 (dd, J=16, 7 Hz, 1H), 2.52 (dd, J=16, 7 Hz, 1H), 2.72 (br.s, 1H), 2.98 (br.s, 1H), 3.28 (s, 3H), 3.29 (br.s, 1H), 4.11 (q, J=7 Hz, 2H), 4.26 (s, 1H), 7.19 (m, 2H), 7.27 (m, 4H), 7.44 (m, 4H).

(1e) Synthesis of 2-((3R*,4S*)-1-benzhydryl-3-methoxypiperidin-4-yl)acetic Acid Ethyl Ester Using a CHIRALPAK OJ-H column, the enantiomers of (±)-2-(cis-1-benzhydryl-3-methoxypiperidin-4-yl)acetic acid ethyl ester (1.127 g) were separated (optical resolution) under the following conditions, to obtain the title compound (0.411 g) as the first eluting fraction.
HPLC Conditions
Column: CHIRAL PAK OJ-H (Lot; OJH-0CJ-FA001), 20 mm×250 mm, 5 μm;
  Mobile phase: Hexane:ethanol=98:2;
  Elution rate: 20 mL/min;
  Concentration: 67 mg/mL;
  Injection amount: 0.3 mL;
HPLC retention time: 10.5 min (first-eluting fraction)
$^1$H-NMR (400 MHz, CDCl$_3$) δ: 1.24 (t, J=7 Hz, 3H), 1.49 (m, 1H), 1.69 (m, 1H), 1.94-2.12 (m, 3H), 2.27 (dd, J=16, 7 Hz, 1H), 2.52 (dd, J=16, 7 Hz, 1H), 2.72 (br.s, 1H), 2.98 (br.s, 1H), 3.27 (s, 3H), 3.29 (br.s, 1H), 4.11 (q, J=7 Hz, 2H), 4.26 (s, 1H), 7.19 (m, 2H), 7.27 (m, 4H), 7.44 (m, 4H).

(1f) Synthesis of 2-((3R*,4S*)-3-methoxypiperidin-4-yl)acetic Acid Ethyl Ester Hydrochloride A mixture of 2-((3R*,4S*)-1-benzhydryl-3-methoxypiperidin-4-yl)acetic acid ethyl ester (411 mg), 1N hydrochloric acid (1.118 mL), palladium-activated carbon (Pd 5%) (0.238 g), cyclohexene (20 mL) and ethanol (80 mL) was stirred at 90° C. for 18 hours. The reaction mixture was filtered through Celite and the Celite was washed with ethanol (50 mL×2). The filtrate and the washing solution were combined and concentrated under reduced pressure. A mixed solvent of heptane and toluene (10 mL, 1:1) and 2N hydrochloric acid (20 mL) were added to the residue and the layers were separated. The organic layer was extracted with 2N hydrochloric acid (20 mL). A 5N sodium hydroxide aqueous solution was added to the combined aqueous layers to alkalize and the layers were extracted with dichloromethane (50 mL×2). The combined organic layers were dried over anhydrous magnesium sulfate. The drying agent was filtered off, a 4N hydrogen chloride ethyl acetate solution (2 mL) was added to the filtrate and concentrated under reduced pressure, to obtain the title compound (119 mg).

$^1$H-NMR (400 MHz, CD$_3$OD) δ: 1.25 (t, J=7 Hz, 3H), 1.72 (m, 1H), 1.76 (m, 1H), 2.20 (m, 1H), 2.34 (dd, J=17, 7 Hz, 1H), 2.52 (dd, J=17, 8 Hz, 1H), 3.02 (m, 2H), 3.27 (m, 1H), 3.41 (s, 3H), 3.60 (m, 2H), 4.14 (q, J=7 Hz, 2H).

Reference Example 2

Synthesis of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid

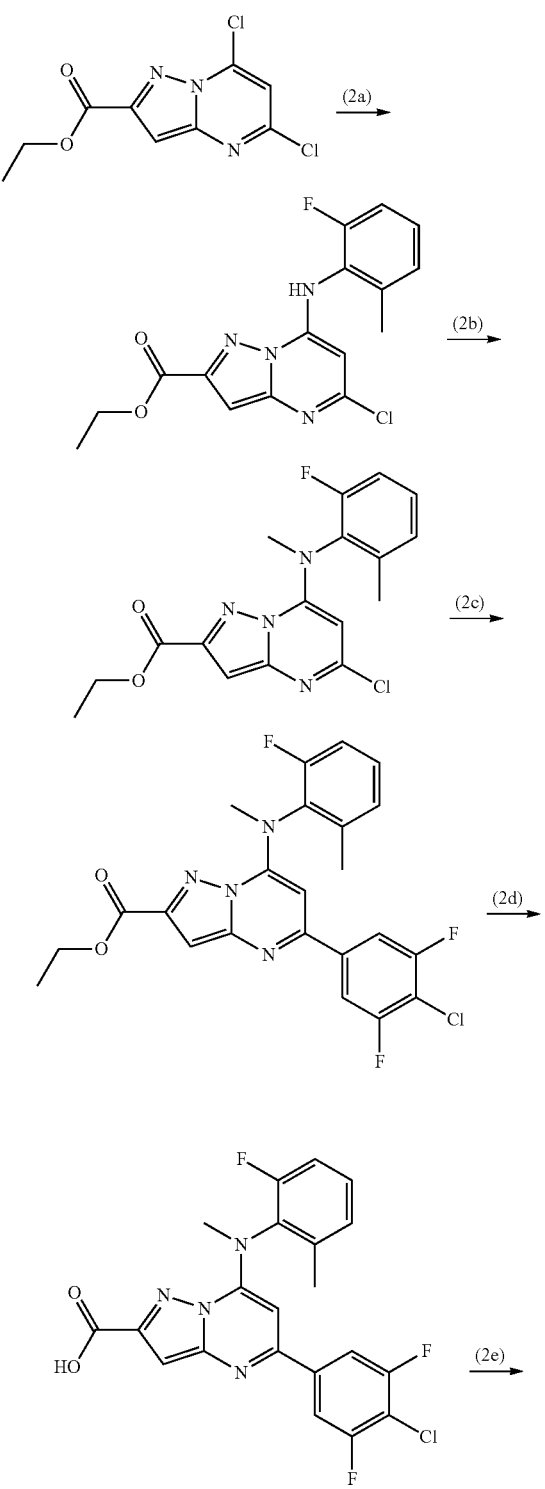

-continued

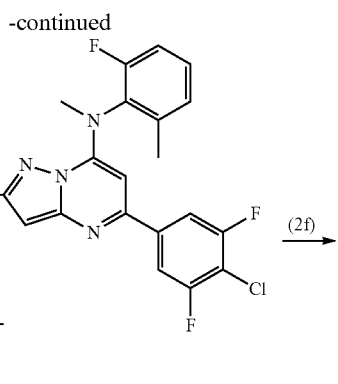

(2f)

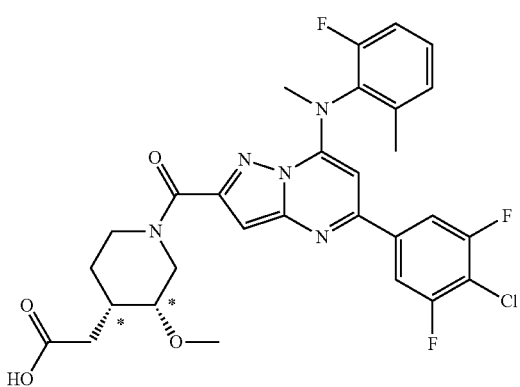 [SMILES: CO[C@H]1CN(C(=O)c2cc3nc(-c4cc(F)c(Cl)c(F)c4)cc(N(C)c4c(C)cccc4F)n3n2)CC[C@H]1CC(=O)O]

(2a) Synthesis of 5-chloro-7-((2-fluoro-6-methylphenyl)amino)pyrazolo[1,5-a]pyrimidine-2-carboxylic Acid Ethyl Ester A solution of 5,7-dichloropyrazolo[1,5-a]pyrimidine-2-carboxylic acid ethyl ester (CAS No. 1232224-62-2) (5 g) and 2-fluoro-6-methylaniline (CAS No. 443-89-0) (2.41 g) in NMP (3 mL) was stirred at 120° C. for 4 hours. The reaction mixture was combined with a reaction solution separately obtained by stirring 5,7-dichloropyrazolo[1,5-a]pyrimidine-2-carboxylic acid ethyl ester (0.50 g) and 2-fluoro-6-methylaniline (0.27 g) in NMP (0.20 mL) at 120° C. for 4 hours, diluted with ethyl acetate, washed with water and saturated saline and dried over anhydrous sodium sulfate. After filtering off the drying agent, the filtrate was concentrated under reduced pressure, dichloromethane was added to the residue and the insoluble solid was collected by filtration, to obtain the title compound (2.88 g) as a light yellow solid. The filtrate was concentrated under reduced pressure and the residue was purified by silica gel column chromatography (hexane-ethyl acetate system), to obtain the title compound (2.28 g).

$^1$H-NMR (400 MHz, CDCl$_3$) δ: 1.46 (t, J=7 Hz, 3H), 2.34 (s, 3H), 4.50 (q, J=7 Hz, 2H), 5.75 (s, 1H), 7.02 (s, 1H), 7.12 (t, J=8 Hz, 1H), 7.18 (br.d, J=8 Hz, 1H), 7.35 (td, J=8, 6 Hz, 1H), 7.82 (br.s, 1H).

(2b) Synthesis of 5-chloro-7-((2-fluoro-6-methylphenyl)(methyl)amino)pyrazolo[1,5-a]pyrimidine-2-carboxylic Acid Ethyl Ester Cesium carbonate (7.23 g) and methyl iodide (4.61 mL) were added to a solution of 5-chloro-7-((2-fluoro-6-methylphenyl)amino)pyrazolo[1,5-a]pyrimidine-2-carboxylic acid ethyl ester (5.16 g) in DMF (80 mL) and stirred at 50° C. for 3 hours. The reaction mixture was diluted with ethyl acetate, washed sequentially with water and saturated saline and dried over anhydrous sodium sulfate. The drying agent was filtered off and the filtrate was concentrated under reduced pressure. The residue was purified by silica gel column chromatography (heptane-ethyl acetate system), to obtain the title compound (4.64 g) as a light yellow solid.

$^1$H-NMR (400 MHz, CDCl$_3$) δ: 1.37 (t, J=7 Hz, 3H), 2.26 (s, 3H), 3.83 (br.s, 3H), 4.36 (q, J=7 Hz, 2H), 5.79 (br.s, 1H), 6.88 (s, 1H), 7.04 (t, J=9 Hz, 1H), 7.13 (d, J=8 Hz, 1H), 7.30 (td, =9, 6 Hz, 1H).

(2c) Synthesis of 5-(4-chloro-3,5-difluorophenyl)-7-((2-fluoro-6-methylphenyl)(methyl)amino)pyrazolo[1,5-a]pyrimidine-2-carboxylic Acid Ethyl Ester Under a nitrogen atmosphere, water (2 mL), sodium carbonate (0.53 g), 4-chloro-3,5-difluorophenylboronic acid (0.44 g) and tetrakis(triphenylphosphine)palladium (0) (0.12 were added to a mixture of 5-chloro-7-((2-fluoro-6-methylphenyl)(methyl)amino)pyrazolo[1,5-a]pyrimidine-2-carboxylic acid ethyl ester (0.73 g) and 1,4-dioxane (16 mL) and stirred at 100° C. for 3 hours. After bringing back to room temperature, ethyl acetate (200 mL) and water (50 mL) were added to the reaction mixture, and the organic layer was separated and dried over anhydrous magnesium sulfate. The drying agent was filtered off and the filtrate was concentrated under reduced pressure. The residue was purified by silica gel column chromatography (heptane-ethyl acetate system), to obtain the title compound (0.96 g) as a light yellow solid.

$^1$H-NMR (400 MHz, CDCl$_3$) δ: 1.39 (t, J=7 Hz, 3H), 2.28 (s, 3H), 3.88 (s, 3H), 4.38 (q, J=7 Hz, 2H), 6.14 (s, 1H), 7.03 (s, 1H), 7.04 (dd, J=9, 8 Hz, 1H), 7.15 (d, J=8 Hz, 1H), 7.32 (td, J=8.6 Hz, 1H), 7.57 (d, J=8 Hz, 2H).

(2d) Synthesis of 5-(4-chloro-3,5-difluorophenyl)-7-((2-fluoro-6-methylphenyl)(methyl)amino)pyrazolo[1,5-a]pyrimidine-2-carboxylic Acid Water (10 mL) and a 4N lithium hydroxide aqueous solution (2.47 mL) were added to a mixture of 5-(4-chloro-3,5-difluorophenyl)-7-((2-fluoro-6-methylphenyl)(methyl)amino)pyrazolo[1,5-a]pyrimidine-2-carboxylic acid ethyl ester (2.35 g) and 1,4-dioxane (100 mL) and stirred at room temperature for 17 hours. 5N Hydrochloric acid (2 mL) was added and the reaction mixture was concentrated under reduced pressure to a volume of about 15 mL. The mixture was sonicated and stirred at room temperature for 30 minutes, subsequently the solid was collected by filtration, washed with water (5 mL) and dried under reduced pressure, to obtain the title compound (2.24 g) as a light yellow solid.

$^1$H-NMR (400 MHz, CDCl$_3$) δ: 2.30 (s, 3H), 3.71 (s, 3H), 6.47 (s, 1H), 7.03 (t, J=9 Hz, 1H), 7.08 (s, 1H), 7.13-7.18 (m, 1H), 7.34 (td, J=8, 5 Hz, 1H), 7.69 (d, J=7 HZ, 2H).

(2e) Synthesis of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid Ethyl Ester HOBT (57 mg), WSC (72 mg), 2-((3R*,4S*)-3-methoxypiperidin-4-yl)acetic acid ethyl ester hydrochloride (77 mg) (Reference Example 1) and triethylamine (101 mg) were added sequentially to a solution of 5-(4-chloro-3,5-difluorophenyl)-7-((2-fluoro-6-methylphenyl(methyl)amino)pyrazolo[1,5-a]pyrimidine-2-carboxylic acid (112 mg) in DMF (6 mL) and stirred at room temperature for 15 hours. Ethyl acetate (50 mL) and water (20 mL) were added to the reaction mixture, and the organic layer was washed with water (20 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (137 mg).

¹H-NMR (500 MHz, CDCl₃, mixture of rotamers) δ: 1.26 (m, 3H), 1.40-1.74 (m, 2H), 2.12-2.55 (m, 5H), 2.60-3.11 (m, 4H), 3.38-3.75 (m, 6H), 4.14 (m, 2H), 4.10-4.46 (m, 1H), 4.54-4.95 (m, 1H), 6.29-6.53 (m, 1H), 6.90-7.28 (m, 4H), 7.61-7.70 (m, 2H).

(2f) Synthesis of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid An aqueous solution (1.5 mL) of lithium hydroxide (10.4 mg) was added to a solution of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid ethyl ester (137 mg) in 1.4-dioxane (6 mL) and stirred at room temperature for 20 hours. DMSO (2 mL) and acetic acid (0.1 mL) were added to the reaction mixture, which was concentrated under reduced pressure. The residue was purified by reverse phase silica gel column chromatography (acetonitrile-water, 0.1% acetic acid system), to obtain the title compound (92 mg) as a white solid.

¹H-NMR (600 MHz, CDCl₃, 30° C., mixture of rotamers) δ: 1.25-1.76 (m, 2H), 2.01-2.41 (m, 414), 2.47-3.14 (m, 4H), 3.38-3.75 (m, 7H), 4.13-4.46 (m, 1H), 4.54-4.98 (m, 1H), 6.29-6.57 (m, 1H), 6.84-7.30 (m, 4H), 7.56-7.79 (m, 2H).

Mass spectrum (ESI) m/z: 602 (M+H)⁺.

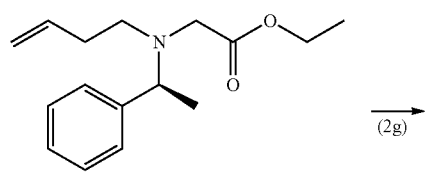

(2g)

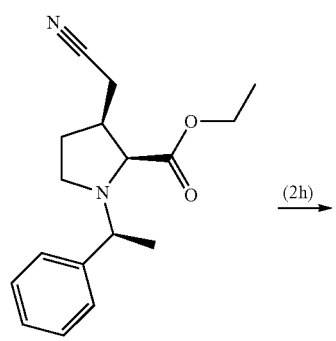

(2h)

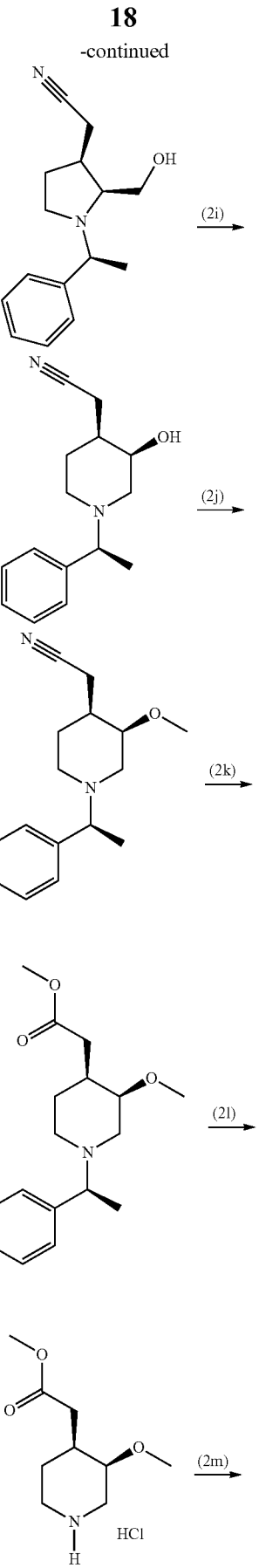

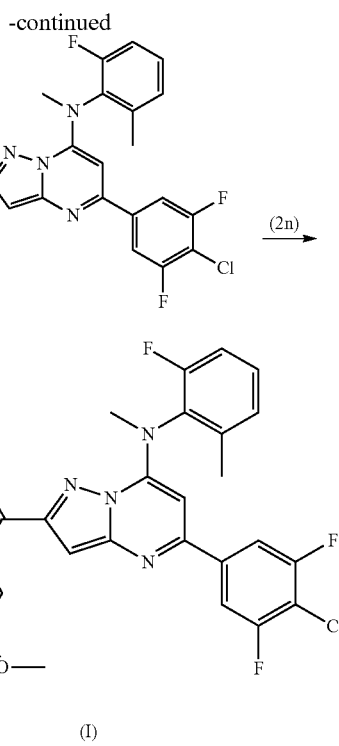

(2g) Synthesis of (2S,3S)-3-(cyanomethyl)-1-((S)-1-phenylethyl)pyrrolidine-2-carboxylic Acid Ethyl Ester Under a nitrogen atmosphere, a solution of (S)-2-(buten-3-en-1-yl(1-phenylethyl)amino)acetic acid ethyl ester (CAS No. 186586-65-2) (60.29 g) in THF (750 mL) was cooled to −75° C. and a solution of lithium diisopropylamide in n-hexane-THF (1.13 M, 245 mL) cooled with ethanol-dry ice was added to the solution using a cannula. After raising the temperature to −20° C. and stirring for 15 minutes, the reaction mixture was subsequently cooled again using a cooling tank with ethanol-dry ice as a refrigerant and a solution of zinc bromide (156 g) in diethyl ether (800 mL) was added at −72° C. or less. The cooling tank was removed to bring the reaction mixture back to room temperature and the solution was stirred for 1 hour. Using a cooling tank with ice water containing salt as a refrigerant, the reaction mixture was cooled to 0° C. or less and a mixture of copper cyanide (I) (41.3 g), lithium chloride (39.1 g) and THF (750 mL) was added. Subsequently, a solution of (4-methylphenyl)sulfonyl cyanide (CAS No. 19158-5H) (50.2 g) in THF (200 mL) was added and stirred at room temperature for 14 hours. While stirring, water (1000 mL), ammonia water (28%, 300 mL) and ethyl acetate (1500 mL) were added. The suspension was filtered through Celite to remove the precipitate. The filtrate was moved to a separatory funnel to separate the organic layer from the aqueous layer and the organic layer was washed sequentially with ammonia water (10%, 750 mL), water (750 mL) and a saturated sodium chloride aqueous solution (750 mL). The Celite and precipitate were washed 4 times with ethyl acetate (500 mL) and these washing solutions were combined Using the combined washing solution, the above 4 aqueous layers (the aqueous layer separated first, the ammonia water used for washing, the water used for washing and the saturated sodium chloride aqueous solution used for washing) were sequentially extracted. The organic layers were all combined and dried over anhydrous magnesium sulfate. The drying agent was filtered off and the filtrate was concentrated under reduced pressure. The residue was purified by silica gel column chromatography (heptane-ethyl acetate system), to obtain the title compound (42.98 g).

$^1$H-NMR (400 MHz, CDCl$_3$, major isomer) δ: 1.24 (t, J=7 Hz, 3H), 1.36 (d, J=7 Hz, 3H), 1.77 (m, 1H), 2.18 (m, 1H), 2.27 (dd, J=17, 9 Hz, 1H), 2.35 (dd, J=17, 7 Hz, 1H), 2.66 (m, 1H), 2.95 (q, J=8 Hz, 1H), 3.10 (td, J=9, 3 Hz, 1H), 3.42 (d, J=8 Hz, 1H), 3.75 (q, J=7 Hz, 1H), 4.09-4.18 (m, 2H), 7.22-7.38 (m, 5H).

(2h) Synthesis of 2-((2 S,3S)-2-hydroxymethyl-1-0 S)-1-phenylethyl)pyrrolidin-3-yl)acetonitrile Under ice cooling and a nitrogen atmosphere, lithium tetrahydroborate (20 g) was added to a solution of (2S,3S)-3-(cyanomethyl)-1-((S)-1-phenylethyl)pyrrolidine-2-carboxylic acid ethyl ester (44.74 g) in THF (700 mL) and heated to reflux for 5 hours. The reaction mixture was cooled to room temperature and was poured into a mixture of 1N hydrochloric acid (1000 mL) and ethyl acetate. The reaction mixture was stirred for 30 minutes, subsequently sodium hydrogen carbonate (about 100 g) was added and extracted with ethyl acetate 3 times and dichloromethane twice. The organic layers were combined and dried, the drying agent was filtered off and subsequently the filtrate was concentrated under reduced pressure. The residue was purified by NH silica gel column chromatography (heptane-ethyl acetate system), to obtain the title compound (28.98 g).

$^1$H-NMR (500 MHz, CDCl$_3$, major isomer) δ: 1.47 (d, J=7 Hz, 3H), 1.59 (qd, J=12, 7 Hz, 1H), 1.93 (dt, J=12, 6 Hz, 1H), 2.32-2.40 (m, 1H), 2.46-2.63 (m, 3H), 3.01 (dd, J=9, 8 Hz, 1H), 3.08-3.10 (m, 1H), 3.27 (d, J=11 Hz, 1H), 3.55 (dd, J=12, 2 Hz, 1H), 3.65 (dd, J=12, 4 Hz, 1H), 3.87 (q, J=7 Hz, 1H), 7.26-7.36 (m, 5H).

(2i) Synthesis of 2-((3R,4S)-3-hydroxy-1-((S)-1-phenylethyl)piperidin-4-yl)acetonitrile Under a nitrogen atmosphere, a solution of 2-((2S,3S)-2-hydroxymethyl-1-((S)-1-phenylethyl)pyrrolidin-3-yl)acetonitrile (52.44 g) in THF (2000 mL) was cooled to −74° C. or less and trifluoroacetic anhydride (36.4 mL) was added dropwise while stirring in such a way that the internal temperature did not exceed −73° C. After further stirring for 3 hours, triethylamine (120 mL) was added dropwise. After stirring for 15 minutes, the internal temperature was brought back to room temperature and the reaction mixture was heated to reflux for 15 hours. The solvent was removed under reduced pressure, ethyl acetate (5000 mL) and a 2N sodium hydroxide aqueous solution (500 mL) were added to the residue to separate the solution. The organic layer was dried over anhydrous magnesium sulfate, the drying agent was filtered off and the filtrate was concentrated under reduced pressure. The residue was purified by NH silica gel column chromatography (heptane ethyl acetate system), to obtain the title compound (51.25 g).

$^1$H-NMR. (400 MHz, CDCl$_3$, major isomer) δ: 1.37 (d, J=7 Hz, 3H), 1.47-1.76 (m, 3H), 1.95 (td, J=12, 3 Hz, 1H), 2.15 (dd, J=12, 1 Hz, 1H), 2.33 (dd, J=17, 8 Hz, 1H), 2.46 (dd, J=17, 7 Hz, 1H), 2.82-2.86 (m, 2H), 3.09-3.14 (m, 1H), 3.56 (q, J=7 Hz, 1H), 3.74 (d, J=10 Hz, 1H), 7.24-7.35 (m, 5H).

(2j) Synthesis of 2-((3R,4S)-3-methoxy-1-((S)-1-phenylethyl)piperidin-4-yl)acetonitrile Under ice cooling and a nitrogen atmosphere, sodium hydride (60%, 9.19 g) was added gradually while stirring over a period of 15 minutes to a mixture of 2-((3R,4S)-3-hydroxy-1-((S)-1-phenylethyl)piperidin-4-yl) acetonitrile (51.01 g) and THF (750 mL). After further stirring for 10 minutes, dimethyl sulfate (22.94 mL) was added dropwise. After stirring for 5 hours, a saturated ammonium chloride aqueous solution (50 mL), ammonia water (28%, 50 mL) and ethyl acetate (1000 mL) were sequentially added and stirred for 30 minutes. A 1N sodium hydroxide aqueous solution (500 mL) was added to separate the solution. The organic layer was washed with a saturated sodium chloride aqueous solution (250 mL) and the combined aqueous layers were extracted with ethyl acetate (500 mL). The organic layers were combined, dried over anhydrous magnesium sulfate, the drying agent was filtered off and the filtrate was concentrated under reduced pressure. The residue was purified by NH silica gel column chromatography (heptane-ethyl acetate system), to obtain the title compound (47.9 g).

$^1$H-NMR (400 MHz, CDCl$_3$, major isomer) δ: 1.38 (d, J=7 Hz, 3H), 1.53-1.59 (m, 1H), 1.63-1.72 (m, 1H), 1.85-1.94 (m, 1H), 2.02-2.15 (m, 2H), 2.30 (dd, J=17, 7 Hz, 1H), 2.49 (dd, J=17, 8 Hz, 1H), 2.74 (br.d, J=11 Hz, 1H), 3.04 (br.d, J=11 Hz, 1H), 3.30 (s, 3H), 3.38 (br.s, 1H), 3.55 (q, J=7 Hz, 1H), 7.23-7.33 (m, 5H).

(2k) Synthesis of 2-((3R,4S)-3-methoxy-1-((S)-1-phenylethyl)piperidin-4-yl)acetic Acid Methyl Ester Under a nitrogen atmosphere, thionyl chloride (352 mL) was added dropwise under ice cooling to methanol (1500 mL), subsequently a solution of 2-((3R,4S)-3-methoxy-1-((S)-1-phenylethyl)piperidin-4-yl)acetonitrile (49.8 g) in methanol (50 mL) was added. The mixture was heated to reflux for 20 hours, subsequently ice cooled, and thionyl chloride (352 mL) was further added dropwise, and heated to reflux for 22 hours. The reaction mixture was ice cooled again, and thionyl chloride (50 mL) was further added dropwise, and heated to reflux for 62 hours. The reaction mixture, after brought back to room temperature, was concentrated under reduced pressure. The residue was dissolved in water (250 mL) and ethyl acetate (250 mL), ammonia water (28%, 50 mL) was added and subsequently a 2N sodium hydroxide aqueous solution was added until pH 11 was achieved. The solution was separated, the aqueous layer was extracted with ethyl acetate (500 mL), the organic layers were combined and dried over anhydrous magnesium sulfate, the drying agent was filtered off and the filtrate was concentrated under reduced pressure, to obtain a residue A.

Next, the aqueous layer was concentrated under reduced pressure and methanol (1000 mL) and concentrated sulfuric acid (50 mL) were added to the residue and heated to reflux for 22 hours. The reaction mixture was brought back to room temperature and adjusted to pH 8 with sodium hydrogen carbonate. The solvent was removed under reduced pressure, the residue was dissolved in ethyl acetate (1000 mL) and water (250 mL), pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue B.

Under a nitrogen atmosphere, thionyl chloride (352 mL) was added dropwise under ice cooling to methanol (1500 mL) and subsequently a solution of the residue A in methanol (100 mL) was added. The mixture was heated to reflux for 22 hours. The reaction mixture was brought back to room temperature, the solvent was removed under reduced pressure, the residue was dissolved in ethyl acetate (1000 mL) and water (250 mL), ammonia water (28%, 50 mL) was added, pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue C.

The aqueous layer obtained in the second reaction post-treatment was concentrated under reduced pressure, methanol (1000 mL) and concentrated sulfuric acid (50 mL) were added to the residue and heated to reflux for 22 hours. The reaction mixture was brought back to room temperature and adjusted to pH 8 with sodium hydrogen carbonate. The solvent was removed under reduced pressure, the residue was dissolved in ethyl acetate (1000 mL) and water (250 mL), pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue D.

The residue B, residue C and residue D were combined, purified by NH silica gel column chromatography (heptane-ethyl acetate system), to obtain crude 2-((3R,4S)-3-methoxy-1-((S)-1-phenylethyl)piperidin-4-yl)acetic acid methyl ester (52.35 g).

A 4N hydrogen chloride ethyl acetate solution (100 mL) was added with stirring to an ethyl acetate (400 mL) solution wherein crude 2-((3R,4S)-3-methoxy-1-((S)-1-phenylethyl) piperidin-4-yl) acetic acid methyl ester (1.45 g) separately obtained by the same method was combined with the crude 2-((3R,4S)-3-methoxy-1-((S)-1-phenylethyl)piperidin-4-yl) acetic acid methyl ester (52.35 g). The reaction mixture was stirred at room temperature overnight, subsequently the precipitate was collected by filtration, washed with ethyl acetate (100 mL) and dried under reduced pressure. Water (250 mL), ethyl acetate (250 mL) and a sodium hydrogen carbonate aqueous solution (250 mL) were added sequentially while stirring to the obtained solid. After further adding ethyl acetate (750 mL), pH was adjusted to 12 using potassium carbonate and the layers were separated. The aqueous layer was washed with ethyl acetate (250 mL), the washing solution and the separated organic layer were combined and dried over anhydrous magnesium sulfate, the drying agent was filtered off and the filtrate was concentrated under reduced pressure. The obtained residue (46.3 g) was dissolved in ethyl acetate (400 mL) and a 4N hydrogen chloride ethyl acetate solution (80 mL) was added while stirring. Water (250 mL) and ethyl acetate (250 mL) were added sequentially and sodium hydrogen carbonate were added while stirring to the solid obtained by stirring the reaction mixture at room temperature overnight, subsequently collecting the precipitate by filtration, washing with ethyl acetate (40 mL) and drying under reduced pressure. Water (750 mL) and ethyl acetate (750 mL) were added to separate the layers. A 5N sodium hydroxide aqueous solution (50 nil) was added to the aqueous layer, which was extracted with ethyl acetate (1000 mL). The organic layers were combined, dried over anhydrous magnesium sulfate, the drying agent was filtered off and the filtrate was concentrated under reduced pressure, to obtain 45.2 g of the residue. The residue was combined with 16.2 g of the residue obtained separately by the same operations, dissolved in ethyl acetate (500 mL) and a 4N hydrogen chloride ethyl acetate solution (100 mL) was added while stirring. The reaction mixture was stirred at room temperature overnight, subsequently the precipitate was collected by filtration, washed twice with ethyl acetate (60 mL) and dried under reduced pressure. Water (800 mL) and ethyl acetate (800 mL) were added sequentially to the solid obtained, sodium hydrogen carbonate was added while stirring and the solution was separated. A 5N sodium hydroxide aqueous solution (50 mL) was added to the aqueous layer, which was extracted with ethyl acetate (800 mL). The organic layers were combined, dried over anhydrous magnesium sulfate, the drying agent was filtered off and the filtrate was concentrated under reduced pressure, to obtain the title compound (60.7 g).

$^1$H-NMR (400 MHz, CDCl$_3$) δ: 1.38 (d, J=7 Hz, 3H), 1.45-1.54 (m, 1H), 1.57-1.67 (m, 1H), 2.03-2.21 (m, 3H), 2.24 (dd, J=16, 7 Hz, 1H), 2.50 (dd, J=16, 7 Hz, 1H), 2.64 (br.s, 1H), 2.85 (br.s, 1H), 3.27 (s, 3H), 3.29-3.32 (m, 1H), 3.52 (q, J=7 Hz, 1H), 3.65 (s, 3H), 7.23-7.33 (m, 5H).

(2l) Synthesis of 2-((3R,4S)-3-methoxypiperidin-4-yl)acetic Acid Methyl Ester Hydrochloride Palladium-activated carbon (Pd 10%) (0.639 g) was added to a mixture of a solution of 2-((3R,4S)-3-methoxy-1-((S)-1-phenylethyl)piperidin-4-yl) acetic acid methyl ester (4.37 g) in methanol (50 mL) and a solution of hydrogen chloride in methanol (5-10%, 30 mL) and stirred at room temperature for 16 hours under a hydrogen atmosphere. Further, palladium-activated carbon (Pd 10%) (0.639 g) was added and stirred at room temperature for 24 hours under a hydrogen atmosphere. Palladium-activated carbon (Pd 0%) (0.639 g) was added and further stirred at room temperature for 24 hours under a hydrogen atmosphere. The mixture was filtered through Celite and the Celite was washed with methanol. The filtrate and the washing solution were combined and concentrated under reduced pressure, to obtain the title compound (3.81 g).

$^1$H-NMR (400 MHz, CD$_3$OD) δ: 1.71-1.85 (m, 2H), 2.16-2.25 (m, 1H), 2.25 (dd, J=16, 7 Hz, 1H), 2.53 (dd, J=16, 7 Hz, 1H), 3.00-3.06 (m, 2H), 3.27 (m, 1H), 3.40 (s, 3H), 3.59-3.63 (m, 2H), 3.67 (s, 3H).

(2m) Synthesis of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid Methyl Ester HOBT (2.280 g) and WSC (3.23 g) were added to a solution of 5-(4-chloro-3,5-difluorophenyl)-7-((2-fluoro-6-methylphenyl(methyl)amino)pyrazolo[1,5-a]pyrimidine-2-carboxylic acid (6.03 g) (Reference Example 2-(2d)) in DMF (100 mL), stirred for 15 minutes, subsequently a solution of 2-((3R,4S)-3-methoxypiperidin-4-yl)acetic acid methyl ester hydrochloride (3.36 g) in DMF (50 mL) and triethylamine (5.64 mL) were added sequentially and stirred at room temperature for 3 hours. Ethyl acetate (700 mL) and water (500 mL) were added to the reaction mixture, and the organic layer was washed twice with water (750 mL) containing a small amount of sodium chloride. The aqueous layer and washing solutions were sequentially extracted with ethyl acetate (750 mL), the organic layers were combined and dried over anhydrous magnesium sulfate. The drying agent was filtered off and the filtrate was concentrated under reduced pressure. The residue was purified by silica gel column chromatography (heptane-ethyl acetate system), to obtain the title compound (5.83 g).

$^1$H-NMR (400 MHz, CDCl$_3$, mixture of rotamers) δ: 1.25-1.75 (m, 2H), 2.05-2.95 (m, 9H), 3.38-3.75 (m, 9H), 4.10-4.46 (m, 1H), 4.54-4.95 (m, 1H), 6.37-6.50 (m, 1H), 6.90-7.28 (m, 4H), 7.64-7.76 (m, 2H).

(2n) Synthesis of 2-((3R,4S)-1-(5-(4-fluoro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid Water (30 mL) and a 4N lithium hydroxide aqueous solution (3.49 mL) were added to a solution of 2-((3R,4S)-1-(5-(4-fluoro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid methyl ester (5.73 g) in 1,4-dioxane (150 mL) and stirred at room temperature for 14 hours. DMSO (10 mL) and formic acid (3 mL) were added to the reaction mixture, which was concentrated under reduced pressure. The residue was purified by reverse phase silica gel column chromatography (acetonitrile-water, 0.1% acetic acid system), to obtain the title compound (5.124 g) as a solid.

$^1$H-NMR (500 MHz, CD$_3$OD, mixture of rotamers) E.: 1.24-1.60 (m, 2H), 2.00-2.47 (m, 4H), 2.48-3.12 (m, 4H), 3.31-3.64 (m, 7H), 4.00-4.34 (m, 1H), 4.34-4.65 (m, 1H), 6.84-6.87 (m, 1H), 6.90-7.35 (m, 4H), 7.98-8.01 (m, 2H).
[α]$_D^{20}$: −109.9° (100 mg, DMSO, 5 mL, 100 mm).

Reference Example 3

X-Ray Diffraction Experiment on 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl) Acetic Acid Solid 2-((3R,4S)-1-(5-(4-chloro-3,5-difluorophenyl)-7-((2-fluoro-6-methylphenyl)(methyl)amino) pyrazolo[1,5-a] pyrimidine-2-carbonyl)-3-methoxypiperidin-4-yl)acetic acid obtained in Reference Example 2-(2n) was dissolved in methanol and recrystallized by the vapor diffusion method with acetonitrile as reservoir. An X-ray diffraction experiment was carried out using the obtained single crystal. Crystallographic data and structural analysis results are shown in Table 1 and the atomic coordinate data are shown in Table 2. These results identified the absolute structure of the title compound.

TABLE 1

| | |
|---|---|
| Measurement temperature | 100K |
| Wavelength | 1.54187 Å |
| Crystal system, space group | Tetragonal system, P4$_1$2$_1$2 |
| Lattice constant | a = 10.07760 (8) Å |
| | c = 56.3508 (7) Å |
| Volume | 5722.88 (10) Å$^3$ |
| Z value, Calculated density | 8, 1.397 g/cm$^3$ |
| Crystal size | 0.2 × 0.2 × 0.1 mm |
| Number of total reflections/ Number of unique reflections | 36332/5658 |
| Completeness | 98.4% |
| Phase determination | Direct method (SHELXT Version 2014/5) |

TABLE 1-continued

| Refinement method | Least-squares method on $F^2$ |
|---|---|
| Number of data/Number of parameters | 5658/383 |
| Goodness of fit | 1.054 |
| R Value (All data) | 0.0558 |
| R Value (I > 2σ (I)) | 0.0549 |
| Flack parameter | 0.021 (5) |
| Maximum and minimum difference peaks | 1.09 and −0.50 e/Å$^3$ |

TABLE 21

| Atom | x | y | z | Beq |
|---|---|---|---|---|
| Cl8 | 0.22435 (12) | 1.18031 (10) | 0.76648 (2) | 3.54 (2) |
| F7 | 0.4747 (3) | 1.0360 (3) | 0.77268 (5) | 3.89 (5) |
| F9 | 0.0801 (3) | 1.0411 (3) | 0.72860 (4) | 3.56 (5) |
| F26 | 0.4086 (5) | 0.2758 (5) | 0.71424 (8) | 7.69 (11) |
| O30 | 0.8904 (3) | 0.5016 (3) | 0.64474 (5) | 2.82 (5) |
| O37 | 0.8890 (3) | 0.1675 (3) | 0.68629 (6) | 3.74 (6) |
| O41 | 1.0257 (3) | −0.2595 (3) | 0.68278 (6) | 3.65 (6) |
| O42 | 0.9183 (3) | −0.2401 (3) | 0.64825 (6) | 3.17 (5) |
| N13 | 0.5061 (3) | 0.5220 (3) | 0.68112 (6) | 2.31 (5) |
| N14 | 0.5701 (3) | 0.4396 (3) | 0.66596 (6) | 2.35 (5) |
| N18 | 0.5449 (3) | 0.7086 (3) | 0.70694 (6) | 2.49 (5) |
| N19 | 0.2959 (3) | 0.4237 (4) | 0.67562 (8) | 3.41 (7) |
| N31 | 0.7970 (3) | 0.2975 (3) | 0.64425 (6) | 2.41 (5) |
| C1 | 0.3639 (4) | 0.8225 (4) | 0.72514 (7) | 2.43 (6) |
| C2 | 0.4429 (4) | 0.8765 (4) | 0.74272 (7) | 2.71 (6) |
| C3 | 0.3979 (4) | 0.9838 (4) | 0.75560 (7) | 2.75 (6) |
| C4 | 0.2756 (4) | 1.0421 (4) | 0.75118 (7) | 2.63 (6) |
| C5 | 0.1986 (4) | 0.9859 (4) | 0.73357 (7) | 2.73 (6) |
| C6 | 0.2383 (4) | 0.8765 (4) | 0.72066 (7) | 2.52 (6) |
| C10 | 0.4149 (4) | 0.7127 (4) | 0.71002 (7) | 2.50 (6) |
| C11 | 0.3251 (4) | 0.6201 (4) | 0.69996 (8) | 2.92 (7) |
| C12 | 0.3707 (4) | 0.5195 (4) | 0.68562 (8) | 2.83 (7) |
| C15 | 0.6980 (4) | 0.4784 (4) | 0.66795 (7) | 2.31 (6) |
| C16 | 0.7161 (4) | 0.5825 (4) | 0.68390 (7) | 2.44 (6) |
| C17 | 0.5904 (4) | 0.6122 (4) | 0.69233 (7) | 2.35 (6) |
| C20 | 0.3443 (4) | 0.2896 (4) | 0.67243 (9) | 3.28 (8) |
| C21 | 0.3962 (5) | 0.2189 (5) | 0.69117 (10) | 3.92 (9) |
| C22 | 0.4368 (5) | 0.0866 (5) | 0.68811 (12) | 4.72 (11) |
| C23 | 0.4222 (6) | 0.0297 (5) | 0.66631 (13) | 5.28 (14) |
| C24 | 0.3727 (5) | 0.0979 (5) | 0.64723 (12) | 4.75 (13) |
| C25 | 0.3334 (4) | 0.2318 (5) | 0.65018 (10) | 3.75 (9) |
| C27 | 0.2849 (4) | 0.3080 (4) | 0.63103 (7) | 2.51 (6) |
| C28 | 0.1509 (5) | 0.4311 (6) | 0.67950 (15) | 6.24 (18) |
| C29 | 0.8015 (4) | 0.4240 (3) | 0.65189 (7) | 2.30 (6) |
| C32 | 0.7215 (4) | 0.1909 (4) | 0.65550 (8) | 2.62 (6) |
| C33 | 0.8179 (4) | 0.0975 (4) | 0.66828 (8) | 3.03 (7) |
| C34 | 0.9203 (4) | 0.0409 (4) | 0.65113 (9) | 3.17 (7) |
| C35 | 0.9901 (4) | 0.1539 (4) | 0.63775 (8) | 3.13 (7) |
| C36 | 0.8918 (4) | 0.2507 (4) | 0.62672 (8) | 2.84 (7) |
| C38 | 0.8171 (6) | 0.1866 (6) | 0.70746 (10) | 4.94 (11) |
| C39 | 1.0218 (5) | −0.0476 (4) | 0.66358 (12) | 4.46 (11) |
| C40 | 0.9887 (4) | −0.1923 (4) | 0.66628 (8) | 3.07 (7) |

Reference Example 4

Recrystallization of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid Water (550 mL) was added to a mixture of 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid (63.5 g) obtained by the same method as the method described in Reference Example 2, tetrahydrofuran (156 mL), acetonitrile (496 mL) and water (65 mL) while stirring at the internal temperature of 95° C. After stirring for 30 minutes, acetonitrile (25 mL) and water (10 mL) were added to dissolve the precipitate. Water (3 mL) was added dropwise, after stirring for 30 minutes, acetonitrile (3 mL) was added dropwise until the solution became clear again. After stirring for 30 minutes, the internal temperature was decreased to 50° C. and the reaction mixture was further stirred for 2 hours. The solid title compound (0.05 g) obtained by the same method as the method described in Reference Example 2 was added, the heating was halted, and the reaction mixture was stirred at room temperature for 3 days after the internal temperature was brought back to room temperature. The mixture was cooled to the internal temperature of −5° C., and the solid was collected by filtration and washed with a 4:1:5 mixed solution of acetonitrile: tetrahydrofuran: water (3×200 mL) cooled using ice water and dried under reduced pressure under a nitrogen gas stream to obtain crystals of the title compound (46.0 g).

Powder X-ray diffractometry diffraction angles (2θ±0.2°): 6.1, 9.9, 11.6, 12.7, 13.9, 17.5, 20.6, 21.1, 23.2, 29.4

$^{13}$C-NMR (100 MHz, solid state) δ (ppm): 15.5, 40.5, 47.1, 54.8, 75.0, 99.7, 132.6, 137.5, 164.5, 174.7

Figure 3:
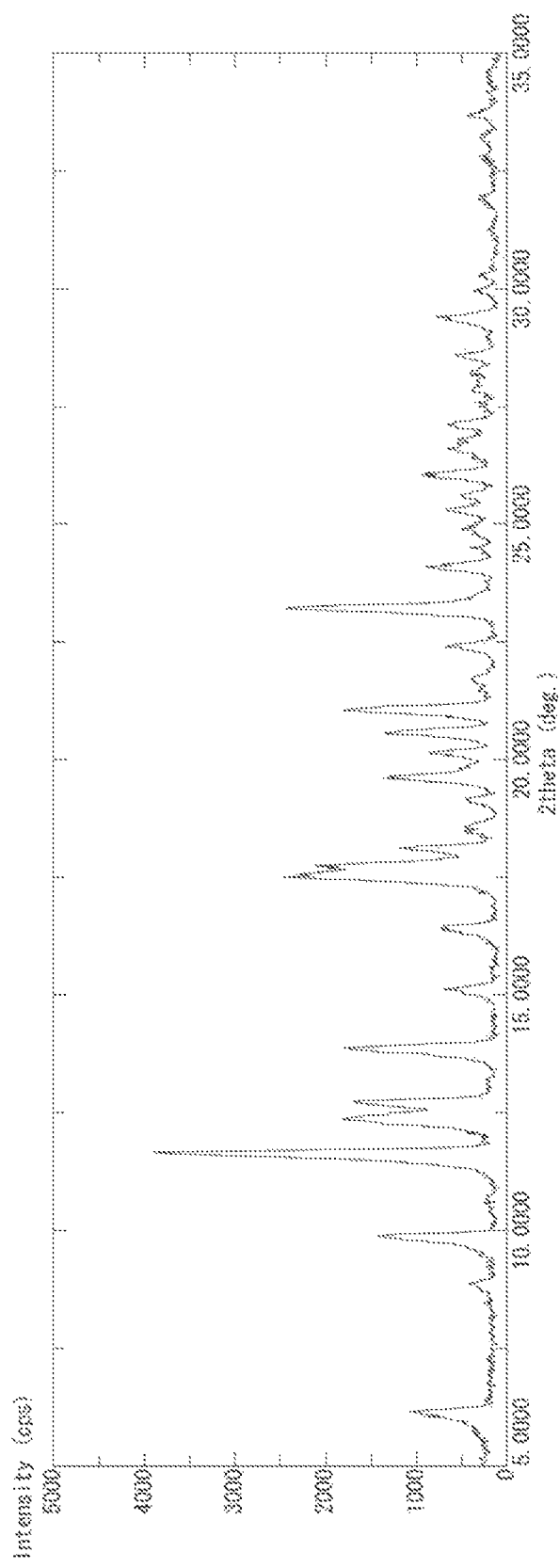
FIG. 3 is a powder X-ray diffraction pattern of crystals of Compound (I) obtained in Reference Example 4. The abscissa shows the diffraction angle (2θ) and the ordinate shows the peak intensity.
Figure 4:
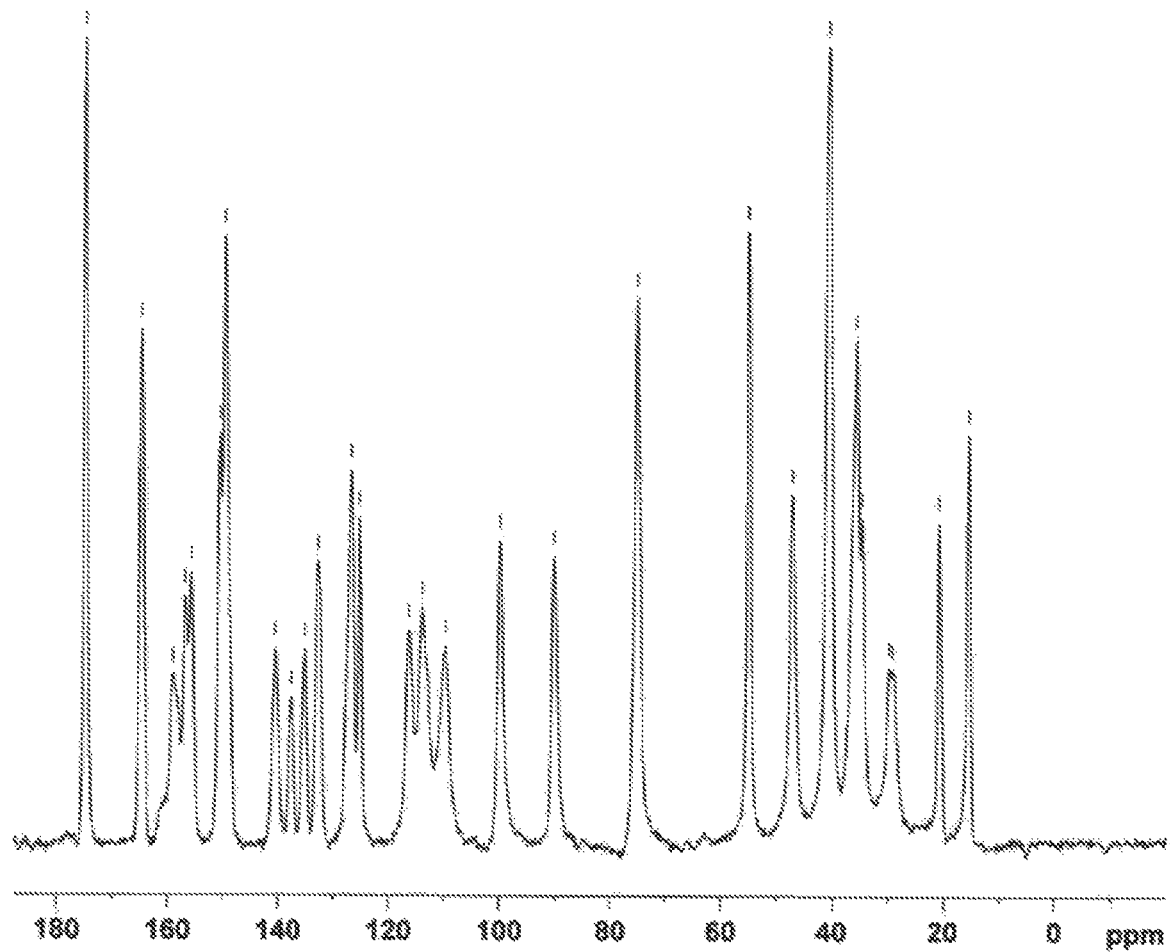
FIG. 4 is a solid state $^{13}$C NMR spectrum of crystals of Compound (I) obtained in Reference Example 4. The abscissa shows the chemical shift (δ) and the ordinate shows the peak intensity.

FIG. 3 shows the powder X-ray diffraction pattern and FIG. 4 shows the solid state $^{13}$C NMR spectrum, of the crystals obtained in Reference Example 4.

Example 1

Synthesis of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic Acid Hydrochloride One mL of ethyl acetate was added to 2-((3R,4S)-1-(5-(4-chloro-3,5-difluorophenyl)-7-((2-fluoro-6-methylphenyl)(methyl)amino) pyrazolo[1,5-a]pyrimidine-2-carbonyl)-3-methoxypiperidin-4-yl)acetic acid (10 mg) obtained by the same method as the method described in Reference Example 2. The solid was completely dissolved in a water bath at 70° C. Three μL of concentrated hydrochloric acid was added and stirred at room temperature overnight. The solid was collected by filtration and dried under reduced pressure to obtain crystals of the title compound (9 mg).

2-((3R,4S)-1-(5-(4-Chloro-3,5-difluorophenyl)-7-((2-fluoro-6-methylphenyl)(meth yl)amino)pyrazolo[1,5-a]pyrimidine-2-carbonyl)-3-methoxypiperidin-4-yl)acetic acid (1.204 g) obtained by the same method as the method described in Reference Example 2 and ethyl acetate (120 mL) were stirred at 70° C. under a nitrogen atmosphere until the solid was completely dissolved. After the solution was brought back to room temperature, a 4N hydrogen chloride ethyl acetate solution (4 mL) and several milligrams of crystals of the title compound obtained above were added. After stirring the solution mixture at room temperature overnight, the solid was collected by filtration, washed with ethyl acetate (5 mL) and dried under reduced pressure to obtain crystals of the title compound (1.202 g).

Powder X-ray diffractometry diffraction angles (2θ±0.2°): 8.3, 11.4, 13.1, 15.2, 15.7, 17.3, 18.8, 19.7, 22.3, 25.0

$^{13}$C-NMR (100 MHz, solid state) δ (ppm): 18.5, 19.9, 56.6, 58.4, 76.2. 77.4, 94.4, 95.9, 129.3, 173.5

Figure 2:
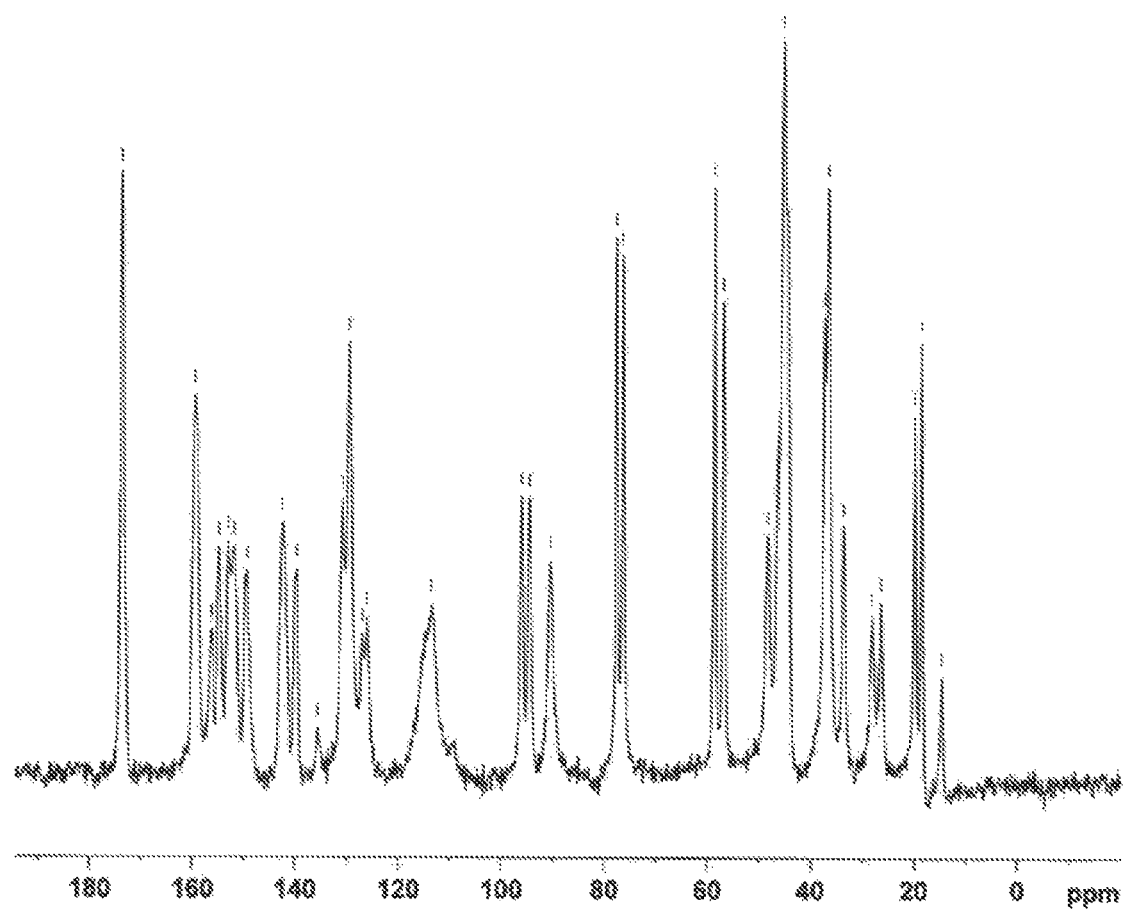
FIG. 2 is a solid state $^{13}C$ NMR spectrum of crystals of a hydrochloride of Compound (I) obtained in Example 1. The abscissa shows the chemical shift (δ) and the ordinate shows the peak intensity.

FIG. 1 shows the powder X-ray diffraction pattern and FIG. 2 shows the solid state $^{13}$C NMR spectrum, of the crystals obtained in Example 1.

Test Example 1 Intracellular Calcium Concentration Measurement

Human embryonic kidney cell line HEK293 cells cultured using DMEM culture medium (Invitrogen) with 3% fetal bovine serum (3% FBS)-added was prepared to have a concentration of $2\times10^5$ cells/mL, and plated in a type I collagen-coated 384-well black plate (clear bottom) (Greiner) so as to be 25 μL/well and cultured in a CO2 incubator overnight. FLIPR Calcium Assay Kit (Molecular Devices) prepared with Hanks-20 mM Hepes buffer (pH 7.4) was added to the cells so as to be 25 μL/well and cultured in the CO2 incubator for 1 hour. Trypsin (SIGMA-ALDRICH, catalog number: T8816, Enzyme Commission Number 3.4.21.4) prepared so as to be 5 U/mL as final concentration (BAEE unit) with Hanks-20 mM Hepes buffer (pH 7.4) was added to a 384-well deep well polypropylene plate (Greiner) to be an agonist reagent plate. Thirty minutes before the measurement using FDSS6000 (Hamamatsu Photonics KK), a test compound prepared with Hanks-20 mM Hepes buffer (pH 7.4) was added to the cell so as to be 8 μL/well. The cell plate to which the test compound was added and the reagent plate were set on FDSS6000, 22 μL/well of the agonist solution was added from the reagent plate, and the change in intracellular calcium concentration was measured with a CCD camera. The measurement was carried out at 37° C. for 120 seconds and the addition of reagent from the reagent plate to the cell plate was carried out using a built-in 384-well automatic dispenser of FDSS6000.

Table 3 shows the inhibitory activity on intracellular calcium elevation (IC50 (nM)) of the test compounds.

TABLE 3

| Test compound | Inhibitory activity on intracellular calcium elevation (IC50 (nM)) |
|---|---|
| Compound (I) | 3.46 |

Test Example 2 Solubility Test

About 1 mg of the test compound was weighed into a test tube and 1 mL of a test solution was added. For the test solutions, a 0.1 M hydrochloric acid aqueous solution (pH 1) and Britton-Robinson buffers (pH 3, pH 5 and pH 7; ionic strength 0.3) were used. The test solution was shaken at room temperature for 24 hours and subsequently filtered through a filter. A concentration of the test compound in the filtrate was measured by high-performance liquid chromatography to evaluate solubility. Table 5 shows the results. Additionally, high-performance liquid chromatography (HPLC) conditions are shown below.
[HPLC Conditions]
Column; YMC-Pack Pro C18, 4.6 mm×35 mm, 3 μm
Mobile phase A; water:acetonitrile:70% perchloric acid=900:100:1
Mobile phase B; water:acetonitrile:70% perchloric acid=100:900:1
Flow rate; 2 mL/min
Column temperature; 40° C.
Detection wavelength; 275 nm
Injection volume; 10 μL
Gradient condition

TABLE 4

| Time (min.) | Mobile phase B (%) |
|---|---|
| 0 | 5 |
| 3 | 90 |

TABLE 4-continued

| Time (min.) | Mobile phase B (%) |
|---|---|
| 5 | 90 |
| 5.1 | 5 |
| 7 | 5 |

TABLE 5

| | | Solubility (mg/mL) | |
|---|---|---|---|
| pH | Test solution | Reference Example 4 | Example 1 |
| 1 | 0.1M hydrochloric acid aqueous solution | <0.001 | 0.004 |
| 3 | Britton-Robinson buffer | <0.001 | <0.001 |
| 5 | Britton-Robinson buffer | <0.001 | 0.001 |
| 7 | Britton-Robinson buffer | 0.013 | >1.2 |

Test Example 3 Dissolution Test

The dissolution test was carried out by the paddle method using FaSSIF (an aqueous solution containing 3 mM sodium taurocholate, 0.75 mM lecithin, 29 mM sodium dihydrogen phosphate and 103 mM potassium chloride and adjusted to pH 6.5 by adding dropwise a sodium hydroxide aqueous solution) as the test solution. About 10 mg of the test compound was added to 100 mL of the test solution. Under the condition at 37° C. and 50 rpm, the test solution was stirred using a paddle. After the start of the stirring, 1 mL of the test solution was collected at each of the time points shown in Table 6 and filtered through a filter. A concentration of the test compound in the filtrate was measured by high-performance liquid chromatography (HPLC conditions were the same conditions described in Test Example 2). Table 6 shows the results.

TABLE 6

| | Concentration of Test compound (mg/mL) | |
|---|---|---|
| Time | Reference Example 4 | Example 1 |
| 10 Min | 0.004 | 0.030 |
| 20 Min | 0.007 | 0.038 |
| 30 Min | 0.008 | 0.046 |
| 40 Min | 0.009 | 0.051 |
| 60 Min | 0.010 | 0.061 |
| 90 Min | 0.011 | 0.072 |
| 120 Min | 0.011 | 0.078 |
| 180 Min | 0.012 | 0.085 |
| 240 Min | 0.012 | 0.087 |
| 24 Hours | 0.018 | 0.103 |

The invention claimed is:

1. A hydrochloride salt of 2-((3R,4S)-1-(5-(4-chloro-3,5-difluorophenyl)-7-((2-fluoro-6-methylphenyl)(methyl)amino)pyrazolo[1,5-α]pyrimidine-2-carbonyl)-3-methoxypiperidin-4-yl)acetic acid represented by the formula (I):

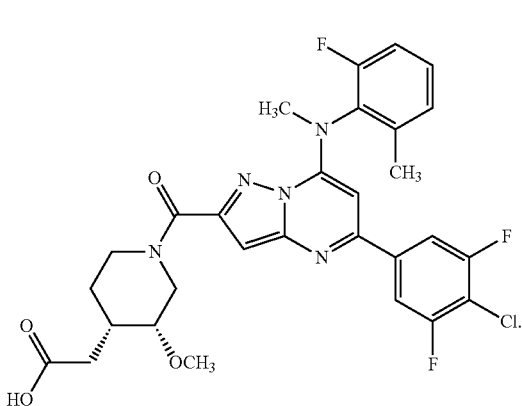

2. A pharmaceutical composition comprising a pharmaceutically acceptable additive and the hydrochloride salt according to claim 1 as an active ingredient.

3. A crystal of a hydrochloride salt of 2-((3R,4S)-1-(5-(4-chloro-3,5-difluorophenyl)-7-((2-fluoro-6-methylphenyl)(methyl)amino)pyrazolo[1,5-α]pyrimidine-2-carbonyl)-3-methoxypiperidin-4-yl)acetic acid represented by the formula (I):

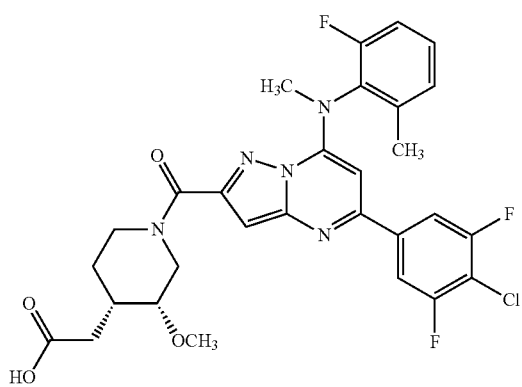

wherein the crystal is characterized by a powder X-ray diffraction pattern comprising a characteristic diffraction peak at a diffraction angle (°2θ) of 8.3°±0.2°θ.

4. The crystal according to claim 3, wherein the crystal is further characterized by a powder X-ray diffraction pattern comprising one additional characteristic diffraction peak at a diffraction angle (°2θ) of 13.1°±0.2°2θ.

5. The crystal according to claim 3, wherein the crystal is further characterized by a powder X-ray diffraction pattern comprising one additional characteristic diffraction peak at a diffraction angle (°2θ) of 15.7°±0.2°2θ.

6. The crystal according to claim 3, wherein the crystal is further characterized by a powder X-ray diffraction pattern comprising two additional characteristic diffraction peaks at diffraction angles (°2θ) of 13.1°±0.2°2θ and 15.7°±0.2°2θ.

7. The crystal according to claim 3, wherein the crystal is further characterized by a powder X-ray diffraction pattern comprising four additional characteristic diffraction peaks at diffraction angles (°2θ) of 11.4°±0.2°2θ, 13.1°±0.2°2θ, 15.7°±0.2°2θ, and 17.3°±0.2°2θ.

8. The crystal according to claim 3, wherein the crystal is further characterized by a powder X-ray diffraction pattern comprising nine additional characteristic diffraction peaks at diffraction angles (°2θ) of 11.4°±0.2°2θ, 13.1°±0.2°2θ, 15.2°±0.2°2θ, 15.7°±0.2°2θ, 17.3°±0.2°2θ, 18.8°±0.2°2θ, 19.7°±0.2°2θ, 22.3°±0.2°2θ, and 25.0°±0.2°2θ.

9. The crystal according to claim 3, wherein the crystal is further characterized by a powder X-ray diffraction pattern as shown in FIG. 1.

10. The crystal according to claim 3, wherein the crystal is further characterized by a solid state $^{13}$C NMR spectrum comprising three characteristic peaks at chemical shifts (δ ppm) of 58.4 ppm±0.5 ppm, 77.4 ppm±0.5 ppm, and 173.5 ppm±0.5 ppm.

11. The crystal according to claim 3, wherein the crystal is further characterized by a solid state $^{13}$C NMR spectrum comprising five characteristic peaks at chemical shifts (δ ppm) of 18.5 ppm±0.5 ppm, 58.4 ppm ±0.5 ppm, 77.4 ppm±0.5 ppm, 94.4 ppm±0.5 ppm, and 173.5 ppm±0.5 ppm.

12. The crystal according to claim 3, wherein the crystal is further characterized by a solid state $^{13}$C NMR spectrum comprising ten characteristic peaks at chemical shifts (δ ppm) of 18.5 ppm ±0.5 ppm, 19.9 ppm ±0.5 ppm, 56.6 ppm±0.5 ppm, 58.4 ppm±0.5 ppm, 76.2 ppm±0.5 ppm, 77.4 ppm±0.5 ppm, 94.4 ppm ±0.5 ppm, 95.9 ppm±0.5 ppm, 129.3 ppm±0.5 ppm, and 173.5 ppm±0.5 ppm.

13. The crystal according to claim 3, wherein the crystal is further characterized by a solid state $^{13}$C NMR spectrum as shown in FIG. 2.

14. A pharmaceutical composition comprising a pharmaceutically acceptable additive and the crystal according to claim 3 as an active ingredient.

* * * * *

UNITED STATES PATENT AND TRADEMARK OFFICE
CERTIFICATE OF CORRECTION

PATENT NO. : 11,312,720 B2
APPLICATION NO. : 16/965067
DATED : April 26, 2022
INVENTOR(S) : Taro Yamashita It is certified that error appears in the above-identified patent and that said Letters Patent is hereby corrected as shown below:

On the Title Page

Column 2, Item (56), OTHER PUBLICATIONS
Line 17, delete "Cytochemistiy," and insert -- Cytochemistry, --.

Column 2, Item (57), ABSTRACT
Line 1, delete "(1)" and insert -- (I) --.

In the Claims

Column 29
Claim 1, Line 4, delete "[1,5-α]" and insert -- [1,5-a] --.
Claim 3, Line 31, delete "[1,5-α]" and insert -- [1,5-a] --.

Column 30
Claim 3, Line 3, delete "0.2°θ." and insert -- 0.2°2θ. --.
Claim 12, Line 41, delete "(6" and insert -- (δ --.

Signed and Sealed this
Second Day of August, 2022

Katherine Kelly Vidal
*Director of the United States Patent and Trademark Office*